(12) United States Patent
Arner et al.

(10) Patent No.: US 7,049,412 B1
(45) Date of Patent: May 23, 2006

(54) ANTIBODIES TO AGGRECAN-DEGRADING METALLOPROTEASE AND DIAGNOSTIC METHODS USING SAME

(75) Inventors: Elizabeth C. Arner, West Grove, PA (US); Timothy C. Burn, Hockessin, DE (US); Robert A. Copeland, Hockessin, DE (US); Carl P. Decicco, Newark, DE (US); Ruiqin Liu, Hockessin, DE (US); Ronald Magolda, Wallingford, PA (US); Michael Pratta, Glassboro, NJ (US); Kimberly A. Solomon, Landenburg, PA (US); Micky D. Tortorella, Newark, DE (US); James M. Trzaskos, Boothwyn, PA (US); Fude Yang, Wilmington, DE (US)

(73) Assignee: Bristol-Myers Squibb Pharma Comp., Princeton, NJ (US)

( * ) Notice: Subject to any disclaimer, the term of this patent is extended or adjusted under 35 U.S.C. 154(b) by 525 days.

(21) Appl. No.: 09/634,287

(22) Filed: Aug. 9, 2000

Related U.S. Application Data

(62) Division of application No. 09/122,126, filed on Jul. 24, 1998, now Pat. No. 6,451,575.

(60) Provisional application No. 60/062,169, filed on Oct. 16, 1997, provisional application No. 60/055,836, filed on Aug. 15, 1997, provisional application No. 60/053,850, filed on Jul. 25, 1997.

(51) Int. Cl.
*C07K 16/00* (2006.01)

(52) U.S. Cl. .............................. 530/388.26; 530/389.1; 435/7.1; 435/7.4

(58) Field of Classification Search ............. 530/130.1, 530/388.26, 389.1; 435/7.1, 7.4
See application file for complete search history.

(56) References Cited

OTHER PUBLICATIONS

Mankin et al., 1970, J. Bone Joint Surg. 52A, 424-434.
Paulson et al. 1987, Biochem. J., 245, 763-772.
Hardingham et al. 1972, Biochem. Biophys. Acta, 279, 401-405.
Heinegard et al. 1974, J. Biol. Chem. 249, 4250-4256.
Hardingham, T. E., 1979, Biochem. J., 177, 237-247.
Flannery et al. 1992, J. Biol. Chem., 267, 1008-1014.
Sandy et al. 1992, J. Clin. Invest., 69, 1512-1516.
Lohmander et al. 1993, Arthritis Rheum., 36, 1214-1222.
Sandy et al. 1991, J. Biol. Chem. 266, 8198.
Sandy et. al. 1991, J. Biol. Chem. 266, 8683-8685.
Loulakis et al. 1992, Biochem. J., 284, 589-593.
Ilic et al. 1992, Arch. Biochem. Biophys., 294, 115-122.
Lark et al. 1995, J. Biol. Chem., 270, 2550-2556.
Fosang et al. 1992, J. Biol. Chem., 267, 19470-19474.
Fosang et al. 1993, Biochem J. 295, 273-276.
Fosang et al. 1996, FEBS Lett. 380, 17-20.
Flannery et al. 1993, Orthop. Trans. 17, 677.
Sandy et al. 1995, Acta Orthop Scand, (Suppl. 266) 66, 26-32.
Fosang et al. 1994, Biochem. J., 305, 347-351.
Walder et al, 1986, Gene 42, 133.
Bauer et al. 1985, Gene 37, 73.
Kunkel, 1985, Proc. Natl. Acad. Sci, USA, 82, 488.
Kunkel et al., 1987, Methods in Enzymol. 154, 367.
Mark et al, 1984, Proc. Natl. Acad. Sci, 18, 5662.
Hopp et al., 1988, Bio/Technology, 6, 1204.
Larsen et al., 1988, J. Biol. Chem, 263, 1023.
Hansen et al., 1988, J. Biol. Chem, 263, 15713.
Larsen et al, 1989, Blood, 73, 1842.
Ashkenazi et al, 1991, PNAS 88, 10535.
Byrn et al, 1990, Nature, 344, 677-670.
Chang et al, 1978, Nature, 275, 617-624.
Goeddel et al, 1979, Nature, 281, 544.
Goeddel et al, 1980, Nucl. Acids Res. 8, 4057.
Maniatis, 1982, Molecular Cloning: A Lab. Manual, Cold Spring Harbor Lab., 412.
Hitzeman et al, 1980, J. Biol. Chem, 255, 12073.
Hess et al. 1968, J. Adv. Enzyme Reg. 7, 149.
Holland et al. 1978, Biochem. 17, 4900.
Fleer et al, 1991, Gene 107, 285-95.
van den Berg et al., 1990, Bio/Technology, 8, 135-139.
Russell et al, 1982, J. Biol. Chem, 258, 2674.
Beier et al, 1982, Nature, 300, 724.
Hinnen et al, 1978, Proc. Natl. Acad. Sci, 75, 1929.
Gluzman et al, 1981, Cell, 23, 175-182.
McMahan et al, 1991, EMBO J. 10, 2821.
Luckow & Summers, 1988, Bio/Technology, 6, 47, 20.
Fiers et al, 1978, Nature, 273, 113.
Urdal et al, 1984, J. Chromatog, 2K, 171.
Stein & Cohen, 1988, Cancer Res. 48, 2659.
van der Krol et al., 1988, BioTechniques, 6, 958.
Hughes et al, 1995, J. Biochem., 306, 799-804.
Scatchard et al, 1949, Ann. N.Y. Acad, Sci, 51, 660.
Hascall et al, 1969, J. Biol. Chem., 244, 2384-2396.
Kuno et al, 1997, J. Biol. Chem. 272, 556-562.
Arner et al., 1997, J. Biol. Chem. 272 (14), 9294-9299.
Kuno et al., 1997, J. Biol. Chem. 272, (1), 556-562.

(Continued)

*Primary Examiner*—Patrick J. Nolan
(74) *Attorney, Agent, or Firm*—Keith R. Lange

(57) ABSTRACT

The invention is directed to the family of aggrecan degrading metallo proteases (ADMPs) that exhibit the ability to cleave the aggrecan core protein between amino acid residues $Glu^{373}$-$Ala^{374}$. The invention encompasses the nucleic acids encoding such enzymes, processes for production of recombinant ADMPs, compositions containing such enzymes, and the use of these enzymes in various assays and for the development of novel inhibitors for use as therapies for diseases involving aggrecanase-mediated degradation of cartilage or other aggrecanase-associated diseases.

3 Claims, No Drawings

OTHER PUBLICATIONS

EMBL/Genbank Databases Accession no D45652, Sequence reference HSG02848 Feb. 11, 1995, Kohichi I. "An expression profile of active genes in human lung."

EMBL/Genbank Databases Accession no W81870, Sequence reference MM87036 Jun. 27, 1996, Marra M. et al. "The WasU-HHMI Mouse EST Project."

EMBL/Genbank Databases Accession no AA288689, Sequence reference MMAA88689, Apr. 16, 1997, Marra M. et al. "The WasU-HHMI Mouse EST Project."

EMBL/Genbank Databases Accession no AB014588, Sequence reference AB014588, Jul. 15, 1998, Ishikawa K et al. "Prediction of the coding sequences of unidentified human genes."

EMBL/Genbank Databases Accession no AA671786, Sequence reference AA671786, Nov. 27, 1997, Marra M. et al. "The WasU-HHMI Mouse EST Project."

J D Sandy, J Westling, R D Kenagy, M L Iruela-Arispe, C Verscharen, J C Rodriguez-Mezaneque, D R Zimmermann, J M Lemire, J W Fischer, T N Wight, A W Clowes, "Versican V1 Proteolysis in Human Aorta in vivo occurs at the Glu441-Ala442 Bond, a Site That is Cleaved by Recombinant ADAMTS-1 and ADAMTS-4", J. Biol. Chem. 276. (16); 13372-13378, Apr. 20, 2001.

M A. Pratta, M D. Tortorella, and E C Arner "Age-related Changes in Aggrecan Glycosylation Affect Cleavage by Aggrecanase" J. Biol. Chem. 275 (50): 39096-39102. Dec. 15, 2000.

JD Sandy, J Westling, RD Kenagy, ML Iruela-Arispe, C Verscharen, JC Rodriguez-Mezaneque, DR Zimmerman, JM Lemire, JW Fischer, TN Wright, AW Clowes, "Versican V1 proteolysis in human aorta in vivo occurs at the Glu441-Ala442 bond, a site that is cleaved by recombinant ADAMTS-1 and ADAMTS-4", J. Biol. Chem. 275 (50): 39096-39102. Dec. 15, 2000.

M.A. PRATTA, M.D. TORTORELLA, AND E C ARNER "Age-related Changes in Aggrecan Glycosylation Affect Cleavage by Aggrecanase"J. Biol. Chem. 275 (50): 39096-39102. Dec. 15, 2000.

ANTIBODIES TO AGGRECAN-DEGRADING METALLOPROTEASE AND DIAGNOSTIC METHODS USING SAME

CROSS REFERENCE TO EARLIER FILED APPLICATION

This application is a division of U.S. Ser. No. 09/122,126, filed Jul. 24, 1998, now issued as U.S. Pat. No. 6,451,575. This application claims the benefit of U.S. Provisional Application No. 60/053,850 filed on Jul. 25, 1997 and U.S. Provisional Application No. 60/055,836 filed on Aug. 15, 1997 and U.S. Provisional Application No. 60/062,169 (unknown at filing), filed on Oct. 16, 1997.

FIELD OF THE INVENTION

The invention is directed to the family of proteins that exhibit aggrecanase activity, the nucleic acids encoding such enzymes, processes for production of recombinant aggrecanases, compositions containing such enzymes, antibodies raised against these enzymes, and the use of these enzymes or antibodies in various assays and therapies.

BACKGROUND OF THE INVENTION

Aggrecan is the major proteoglycan of cartilage and provides this tissue with its mechanical properties of compressibility and elasticity. In arthritic conditions one of the earliest changes observed in cartilage morphology is the depletion of aggrecan [Mankin et al. (1970) J. Bone Joint Surg. 52A, 424–434], which appears to be due to an increased rate of degradation.

The aggrecan molecule is composed of two N-terminal globular domains, G1 and G2, which are separated by an approximately 150 residue interglobular domain (IGD), followed by a long central glycosaminoglycan (GAG) attachment region and a C-terminal globular domain, G3 [Hardingham et al. (1992) in Articular Cartilage and Osteoarthritis: Aggrecan, The Chondroitin Sulfate/Keratin Sulfate Proteoglycan from Cartilage (Kuettner et al.) pp. 5–20, Raven Press, New York and Paulson et al. (1987) Biochem. J. 245, 763–772]. These aggrecan molecules interact through the G1 domain with hyaluronic acid and a link protein to form large molecular weight aggregates which are trapped within the cartilage matrix [Hardingham et al. (1972) Biochim. Biophys. Acta 279, 401–405, Heinegard et al. (1974) J. Biol. Chem. 249, 4250–4256, and Hardingham, T. E. (1979) Biochem. J. 177, 237–247]. Loss of aggrecan from cartilage in arthritic conditions involves proteolytic cleavage of the aggrecan core protein within the IGD, producing a N-terminal G-1 fragment that remains bound to hyaluronic acid and the link protein within the matrix, releasing a large C-terminal GAG-containing aggrecan fragment that diffuses out of the cartilage matrix. Loss of the C-terminal fragment results in cartilage deficient in its mechanical properties. This deficiency arises because the GAGs are the components of aggrecan that impart the mechanical properties to the molecule through their high negative charge and water binding capacity.

Two major sites of proteolytic cleavage have been identified within the IGD, one between amino acid residues $Asn^{341}$-$Phe^{342}$ and the other between amino acid residues $Glu^{373}$-$Ala^{374}$. Although G1 fragments formed by cleavage at the $Asn^{341}$-$Phe^{342}$ site and at the $Glu^{373}$-$Ala^{374}$ site have been identified within articular cartilage [Flannery et al. (1992) J. Biol. Chem. 267, 1008–1014], the N-terminus identified on the large GAG-containing aggrecan C-terminal fragments in synovial fluids of patients with osteoarthritis [Sandy et al. (1992) J. Clin. Invest. 69, 1512–1516], inflammatory joint disease [Lohmander et al. (1993) Arthritis Rheum. 36, 1214–1222] and in the media from cartilage explant and chondrocyte cultures stimulated with interleukin-1 or retinoic acid [Sandy et al. (1991) J. Biol. Chem. 266, 8198., Sandy et al. (1991) J. Biol. Chem. 266, 8683–8685., Loulakis et al. (1992) Biochem. J. 264, 589–593., Ilic et al. (1992) Arch. Biochem. Biophys. 294, 115–122., Lark et al. (1995) J. Biol. Chem. 270, 2550–2556.] was ARGSVIL, indicating that they were formed by cleavage between amino acid residues $Glu^{373}$-$Ala^{374}$. These observations suggest that cleavage at this site may be responsible for cartilage degradation.

Although many matrix metalloproteases (MMP-1, -2, -3, -7, -8, -9 and 13) have been shown to cleave in vitro at the $Asn^{341}$-$Phe^{342}$ site, digestion of aggrecan with a number of these purified proteases has not resulted in cleavage at the $Glu^{373}$-$Ala^{374}$ site [Fosang et al. (1992) J. Biol. Chem. 267, 19470–19474., Flannery et al. (1992) J. Biol. Chem. 267, 1008–1014., Fosang et al. (1993) Biochem. J. 295, 273–276., Fosang et al. (1996) FEBS Lett. 380, 17–20., Flannery et al. (1993) Orthop. Trans. 17, 677., and Fosang et al. (1994) Biochem. J. 305, 347–351]. Therefore, cleavage at this site has been attributed to a novel, proteolytic activity, "aggrecanase".

In addition to the $Glu^{373}$-$Ala^{374}$ bond within the interglobular domain of aggrecan, four potential aggrecanase-sensitive sites have been identified within the C-terminus of the aggrecan core protein [Loulakis et al. (1992) Biochem. J. 264, 589–593. and Sandy et al. (1995) Acta Orhtop Scand (Suppl 266) 66, 26–32]. Although cleavage at these sites which are not within the interglobular domain would not be expected to release the major portion of the aggrecan molecule from the matrix, they may be involved in earlier processing of aggrecan within the matrix.

SUMMARY OF THE INVENTION

The invention encompasses a novel family of biologically active aggrecan degrading metallo proteases ("ADMP") capable of cleaving the aggrecan monomer core protein at the $Glu^{373}$-$Ala^{374}$ aggrecanase site, as isolated and purified polypeptides. An object of the invention covers novel sequences of nucleic acids which encode for members of the ADMP family, and to expression vectors containing cDNA which encodes for novel members of the ADMP family. Another object of the invention is host cells that have been transfected or transformed with expression vectors which contain cDNA that encodes for the ADMP family of polypeptides, and processes for producing members of the ADMP family by culturing such host cells under conditions conducive to expression of an ADMP. Another object of the invention is probes containing nucleic acid sequences that hybridize to a native ADMP nucleotide sequence and the use of these probes for detection of message for an ADMP in biological samples. A further object of the invention is antibodies raised against an ADMP, which may be created as a result of the purification and isolation of members of the ADMP family and the use of such antibodies for the detection of ADMPs in biological samples. Assays utilizing an ADMP to screen for its potential inhibitors are another object of this invention. Members of the ADMP family used to design novel inhibitors of proteases exhibiting aggrecanase activity are also part of the instant invention.

Members of the ADMP family are capable of cleaving the aggrecan monomer core protein at the $Glu^{373}$-$Ala^{374}$ site, but do not readily cleave aggrecan at the $Asn^{341}$-$Phe^{342}$, MMP-sensitive cleavage site, and the zymogen form of the protein consists of the following domains: a propeptide domain containing a furin site, a metalloprotease domain, a disintegrin-like domain and a thrombospondin homologous domain.

As used herein, the term "zymogen" refers to the latent, full-length protein synthesized by the cells and further processed to a catalytically active form, the term "propeptide domain" refers to the N-terminal region of the molecule which contains a cysteine residue involved in latency of the protein, the term "furin cleavage site" refers to a region of the molecule containing a tetra basic sequence of amino acids susceptible to cleavage by furin or furin-like proteases, the term "metalloprotease domain" refers to a region of the molecule which contains a zinc-binding motif with the consensus sequence, HExxHxxGxxH, responsible for the catalytic activity of the protein, the term "disintegrin-like domain" refers to a region of the molecule which exhibits sequence similarity to the disintegrin family of anti-coagulant peptides found in snake venoms, which are characterized by a high cysteine content and have the ability to disrupt cell-matrix interaction, and the term "thrombospondin homologous domain" refers to a region of the molecule containing one or more thrombospondin type 1 (TSP1) motifs with sequence homologous to the amino acid sequence of TSP1 repeats which are conserved in thrombospondin 1 and 2 and have been implicated in the interaction of thrombospondin with sulfated glycoconjugates such as heparin and heparan sulfate.

The first isolated and purified ADMP family member according to the invention, referred to as "ADMP-1", has a molecular weight between about 50 kD and about 98 kD as determined by SDS-polyacrylamide gel electrophoresis (SDS-PAGE). More specifically, the isolated active ADMP-1 was found to have a molecular weight of approximately 67 kD as determined by SDS-PAGE. The isolated and purified metalloprotease of the invention is capable of cleaving the aggrecan monomer core protein at the $Glu^{373}$-$Ala^{374}$ site, but does not readily cleave aggrecan at the $Asn^{341}$-$Phe^{342}$, MMP cleavage site and consists of the following domains: a propeptide domain containing a furin site, a metalloprotease domain, a disintegrin-like domain and a thrombospondin homologous domain. The cDNA sequence of ADMP-1 is shown in SEQ ID NO:1. The isolated and purified ADMP-1 zymogen constitutes amino acids 1–837 of SEQ ID NO:2 and has a molecular weight of about 98 kDa as determined by SDS-PAGE.

The second isolated and purified aggrecanase according to the invention, referred to as "ADMP-2", has a molecular weight between about 45 kD and about 93 kD as determined by SDS-PAGE. More specifically the isolated active ADMP-2 was found as four forms of the same gene product having molecular weights of approximately 50 kD, 54 kD, 62 kD and 64 kD as determined by SDS-PAGE. This second isolated and purified metalloprotease of the invention is capable of cleaving the aggrecan monomer core protein at the $Glu^{373}$-$Ala^{374}$ site, but does not readily cleave aggrecan at the $Asn^{341}$-$Phe^{342}$, MMP cleavage site. The cDNA sequence of ADMP-2 is shown in SEQ ID NO:14. The isolated and purified ADMP-2 zymogen constitutes amino acids 1–930 of SEQ ID NO:15 and has a molecular weight of about 93 kDa as determined by SDS-PAGE.

The instant invention describes a method for treating a mammal having a disease characterized by an overproduction or an upregulated production of an ADMP. This treatment involves administration of a composition containing an efficacious amount of a compound that inhibits the proteolytic activity of members of the ADMP family. These enzymes include, but are not limited to, those containing the sequence of amino acids 1–837 of SEQ ID NO:2 or the sequence of amino acids from 1–930 of SEQ ID NO:15.

The potency of compounds in inhibiting soluble, active ADMP activity in conditioned media from interleukin-1-stimulated bovine nasal cartilage, correlates with their potency in inhibiting cartilage aggrecan cleavage and release from cartilage. This ADMP activity is monitored using an enzymatic assay employing purified aggrecan substrate. Specific products of aggrecanase-mediated cleavage are detected by Western analysis using the monoclonal neoepitope antibody, BC-3 [Hughes et al., Biochem. J. 306:799–804 (1995)]. This antibody recognizes the newly-formed amino-terminal sequence $NH_2$-ARGSVIL on fragments produced by cleavage at the $Glu^{373}$-$Ala^{374}$ aggrecanase site. The term "neoepitope antibody" refers to an antibody which specifically recognizes a new N-terminal amino acid sequence or new C-terminal amino acid sequence generated by proteolytic cleavage but does not recognize these same sequences of amino acids when they are present within the intact protein.

Aggrecanase-mediated degradation of cartilage aggrecan has been implicated in osteoarthritis, joint injury, reactive arthritis, acute pyrophosphate arthritis (pseudogout), psoriatic arthritis and juvenile rheumatoid arthritis. Inhibitors of ADMPs would prevent cleavage of the aggrecan core protein, thereby decreasing the loss of aggrecan from the cartilage. The instant invention contains such an embodiment and also describes a method of inhibiting the cleavage of aggrecan in cartilage of a mammal by administering an efficacious amount of a compound that inhibits the aggrecanase proteolytic activity of an enzyme of the ADMP family. These enzymes include, but are not limited to, those containing the sequence of amino acids from 1–837 of SEQ ID NO:2 or the sequence of amino acids from 1–930 of SEQ ID NO:15.

Inhibitors of members of the ADMP family would be of significant clinical utility and could be potential therapeutic agents for treating the aggrecanase-related disorders cited above. ADMP inhibitors also have clinical utility for the treatment of other conditions characterized by over-production or up-regulated production of an ADMP. Isolation and purification of ADMPs would provide a significant advancement in the treatment of aggrecanase-associated diseases and in the effort to develop inhibitors of these enzymes.

DETAILED DESCRIPTION OF THE INVENTION

Isolated cDNAs encoding human ADMPs are disclosed in SEQ ID NO:1 and SEQ ID NO:14. This discovery of cDNAs encoding human ADMPs enables construction of expression vectors comprising nucleic acid sequences encoding ADMPs, host cells transfected or transformed with the expression vectors, biologically active human ADMPs as isolated and purified proteins, and antibodies immunoreactive with ADMPs.

Isolated and purified ADMP polypeptides according to the invention are useful for detecting the aggrecanase-inhibiting activity of a molecule. In such a method involving routine and conventional techniques, a molecule of unknown aggrecanase-inhibiting activity is mixed with a substrate and incubated with an ADMP polypeptide. The extent of substrate cleavage then can be determined using a neoepitope antibody to detect cleavage fragments generated by specific cleavage at the $Glu^{373}$-$Ala^{374}$ bond.

In addition, ADMP polypeptides according to the invention are useful for the structure-based design of an aggrecanase inhibitor. Such a design would comprise the steps of determining the three-dimensional structure of such ADMP polypeptide, analyzing the three-dimensional structure for the likely binding sites of substrates, synthesizing a molecule that incorporates a predictive reactive site, and determining the aggrecanase-inhibiting activity of the molecule.

Antibodies immunoreactive with ADMPs are now made available through the invention. Such antibodies may be useful for inhibiting aggrecanase activity in vivo and for detecting the presence of an ADMP in a sample.

As used herein, the term "ADMP" refers to a family of polypeptides that are capable of cleaving the aggrecan core protein at the $Glu^{373}$-$Ala^{374}$ bond, but do not readily cleave at the $Asn^{341}$-$Phe^{342}$ bond and consist of the following domains: a propeptide domain containing a furin site, followed by a metalloprotease domain, followed by a disintegrin-like domain, followed by a thrombospondin homologous domain, wherein the polypeptide is either a native or recombinant polypeptide.

The ADMP family encompasses, but is not limited to, proteins having the amino acid sequence 1 to 837 of SEQ ID NO:2 or the sequence of amino acids from 1–930 of SEQ ID NO:15, as well as those proteins having a high degree of similarity (at least 80% homology) with the amino acid sequence 1–837 of SEQ ID NO: 2 or the sequence of amino acids from 1–930 of SEQ ID NO:15 and which proteins are biologically active. In addition, ADMP refers to the biologically active gene products of the nucleotides 405–2919 of SEQ ID NO: 1 and to the biologically active gene products of the nucleotides 121–2910 of SEQ ID NO:14. Further encompassed by the term "ADMP" are the truncated proteins that retain biological activity. Truncated versions are those having less of the C-terminal or N-terminal portion of the protein or that comprise substantially all of the catalytic domain, i.e., amino acids 212–431 of SEQ NO:2 or amino acids 262–479 of SEQ ID NO:15.

The first isolated and purified active aggrecanase according to the invention, referred to as "ADMP-1", has a molecular weight between about 50 kD and about 98 kD as determined by sodium doecyl sulfate-polyacrylamide gel electrophoresis (SDS-PAGE). More specifically, ADMP-1 was found to have a molecular weight of approximately 67 kD as determined by SDS-PAGE. The second isolated and purified active aggrecanase according to the invention, referred to as "ADMP-2", has a molecular weight between about 45 kD and about 93 kD as determined by SDS-PAGE. More specifically, active ADMP-2 was present as four forms of the same gene product found to have molecular weights of approximately 50 kD, approximately 54 kD, approximately 62 kD and approximately 64 kD as determined by SDS-PAGE.

The term "isolated" as used herein, means that an ADMP is essentially free from association with other proteins or polypeptides, for example as a purification product of recombinant host cell culture or as a purified product from a non-recombinant source. The term "substantially purified" as used herein, refers to a mixture that contains an ADMP and is essentially free from association with other proteases, and which substantially purified ADMP retains biological activity. The term "purified ADMP" means that the ADMP is present in a cell-free system. The term "biologically active" as it refers to an ADMP, means that the ADMP is capable of cleaving the aggrecan core protein at the $Glu^{373}$-$Ala^{374}$ bond.

This invention provides a nucleic acid molecule encoding ADMP-1 (SEQ ID NO:1) and ADMP-2 (SEQ ID NO:14). Examples of nucleic acid molecules are RNA, cDNA or isolated genomic DNA molecules. One means of isolating an ADMP is to probe a cDNA or genomic library with a natural or artificial DNA probe derived from the ADMP-1 or ADMP-2 cDNA. DNA probes derived from the ADMP-1 or ADMP-2 cDNA can be used to obtain complementary cDNA, RNA or genomic clones from human, mammalian or other sources, using methods known in the art (such as those outlined in Sambrook et al., *Molecular Cloning: A Laboratory Manual*, 2nd ed., Cold Spring Harbor Laboratory, Cold Spring Harbor, N.Y. (1989)).

A "nucleotide sequence" refers to a polynucleotide molecule in the form of a separate fragment or as a component of a larger nucleic acid construct, that has been derived from DNA or RNA isolated at least once in substantially pure form (i.e., free of contaminating endogenous materials and in a quantity or concentration enabling identification, manipulation, and recovery of its component nucleotide sequences by biochemical methods (such as those outlined in Sambrook et al., *Molecular Cloning: A Laboratory Manual*, 2nd ed., Cold Spring Harbor Laboratory, Cold Spring Harbor, N.Y. (1989)). Such sequences are preferably provided in the form of an open reading frame uninterrupted by internal non-translated sequences, or introns, that are typically present in eukaryotic genes. Sequences of non-translated DNA may be present 5' or 3' from an open reading frame, where the same do not interfere with manipulation or expression of the coding region.

The term "aggrecan degrading metallo protease" ("ADMP") as referred to herein, means a polypeptide substantially homologous to a native ADMP which is biologically active, and an amino acid sequence different from that of the native ADMP (human, bovine, canine, murine or other species) because of one or more deletions, insertions or substitutions. The term includes a variant sequence wherein the variant amino acid sequence preferably is at least 80% identical to a native ADMP amino acid sequence. The percent identity may be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358,1979; (2) a penalty of 3.0 for each gap and an additional 0.10 penalty for each symbol in each gap; and (3) no penalty for end gaps.

"Variants" as referred to herein comprise conservatively substituted sequences, meaning that a given amino acid residue is replaced by a residue having similar physiochemical characteristics. Conservative substitutions are well known in the art and include substitution of one aliphatic residue, such as Ile, Val, Leu, or Ala for another, or substitutions of one polar residue for another, such as between Lys and Arg, Glu and Asp, or Gln and Asn. Conventional procedures and methods can be used for making and using such variants. Other such conservative substitutions, for example, substitutions of entire regions having similar hydrophobicity characteristics, are well known and routinely performed. Naturally occurring ADMP variants are also encompassed by the invention. Examples of such variants are proteins that result from alternate mRNA splicing events or from proteolytic cleavage of an ADMP, wherein the aggrecanase proteolytic property is retained. Alternate splicing of mRNA may yield a truncated but biologically active ADMPs. Variations attributable to proteolysis include, for example, differences in the N- or C-termini upon expression in different types of host cells, due to proteolytic removal of one or more terminal amino acids from the ADMP.

As stated above, the invention provides isolated and purified, or homogeneous, ADMP polypeptides, both recombinant and non-recombinant. Variants and derivatives of native ADMPs that retain the desired biological activity may be obtained by mutations of nucleotide sequences coding for native ADMP polypeptides. Alterations of the native amino acid sequence may be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed procedures can be employed to provide an altered gene wherein predetermined codons can be altered by substitution, deletion or insertion. Exemplary methods of making the alterations set forth above are disclosed by Walder et al. (*Gene* 42:133, 1986); Bauer et al. (*Gene* 37:73, 1985); Craik (*BioTechniques, Jan.* 1985, 12–19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and Mark et al. (*Proc. Natl. Acad. Sci. USA* 18:5662, 1984) all of which are incorporated by reference.

An ADMP may be modified to create ADMP derivatives by forming covalent or aggregative conjugates with other chemical moieties, such as glycosyl groups, polyethylene glycol (PEG) groups, lipids, phosphate, acetyl groups and the like. Covalent derivatives of an ADMP may be prepared by linking the chemical moieties to functional groups on the ADMP amino acid side chains or at the N-terminus or C-terminus of an ADMP polypeptide. Other derivatives of an ADMP within the scope of this invention include covalent or aggregative conjugates of an ADMP or its fragments with other proteins or polypeptides, such as by synthesis in recombinant culture as N-terminal or C-terminal fusions. For example, the conjugate may comprise a signal or leader polypeptide sequence (e.g. the a-factor leader of *Saccharomyces*) at the N-terminus of an ADMP polypeptide. The signal or leader peptide co-translationally or post-translationally directs transfer of the conjugate from its site of synthesis to a site inside or outside of the cell membrane or cell wall.

ADMP polypeptide conjugates can comprise peptides added to facilitate purification and identification of the ADMP. Such peptides include, for example poly-His or the antigenic identification peptides described in Hopp et al., *Bio/Technology.* 6:1204, 1988. The term "ADMP derivative" refers to an ADMP polypeptide conjugated with a chemical moiety, other proteins or polypeptides encompassing, but not limited to, glycosyl groups, polyethylene glycol (PEG) groups, lipids, phosphate, acetyl groups, poly-His peptides, antigenic-identification peptides, signal peptides or leader peptides.

The invention further includes ADMP polypeptides with or without associated native-pattern glycosylation. An ADMP expressed in yeast or mammalian expression systems (e.g., COS-7 cells) may be similar to or significantly different from the native ADMP polypeptide in molecular weight and glycosylation pattern, depending upon the choice of expression system. Expression of ADMP polypeptides in expression systems, such as *E. coli*, provides non-glycosylated molecules. Glycosyl groups may be removed through conventional methods, in particular those utilizing glycopeptidase. In general, a glycosylated ADMP may be incubated with a molar excess of glycopeptidase.

Equivalent DNA constructs that encode various additions or substitutions of amino acid residues or sequences, or deletions of terminal or internal residues or sequences not needed for biological activity, are encompassed by the invention. For example, N-glycosylation sites in the ADMP extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. Appropriate substitutions, additions or deletions to the nucleotide sequence encoding these triplets will result in prevention of attachment of carbohydrate residues at the Asn side chain. Alteration of a single nucleotide, chosen so that Asn is replaced by a different amino acid for example, is sufficient to inactivate the N-glycosylation site. Known procedures for inactivating N-glycosylation sites in proteins include those described in Larsen et al. (*J. Biol. Chem.* 263:1023, 1988), Hansen et al. (*J. Biol. Chem.* 263:15713, 1988) and Larsen et al. (*Blood* 73:1842, 1989), hereby incorporated by reference.

In another example, sequences encoding Cys residues that are not essential for biological activity can be altered to cause the Cys residues to be deleted or replaced with other amino acids, preventing formation of incorrect intramolecular disulfide bridges upon renaturation. Other equivalents may be prepared by modification of adjacent dibasic amino acid residues to enhance expression in yeast systems in which protease activity is present.

Nucleic acid sequences within the scope of the invention include isolated DNA and RNA sequences that hybridize to the native ADMP nucleotide sequences disclosed herein or those of other members of the ADMP family under conditions of moderate or high stringency, and which encode a biologically active ADMP. Conditions of moderate stringency, as known to those having ordinary skill in the art, and as defined by Sambrook et al. *Molecular Cloning: A Laboratory Manual,* 2 ed. Vol. 1, pp. 101–104, Cold Spring Harbor Laboratory Press, (1989), include use of a prewashing solution of 5×SSC, 0.5% SDS, 1.0 mM EDTA (pH 8.0) and hybridization conditions of about 50° C.–60° C., 5×SSC, overnight, preferably 55° C. Conditions of high stringency include higher temperatures of hybridization and washing. The skilled artisan will recognize that the temperature and wash solution salt concentration may be adjusted as necessary according to factors such as the length of the probe.

Due to the known degeneracy of the genetic code wherein more than one codon can encode the same amino acid, a DNA sequence may vary from that shown in SEQ ID NO:1 and still encode an ADMP having the amino acid sequence of SEQ ID NO:2 or a DNA sequence may vary from that shown in SEQ ID NO:14 and still encode an ADMP having the amino acid sequence of SEQ ID NO:15. Such variant DNA sequences may result from silent mutations (e.g., occurring during PCR amplification), or may be the product of deliberate mutagenesis of a native sequence.

The invention thus provides equivalent isolated DNA sequences encoding biologically active ADMPs, selected from: (a) the coding region of a native ADMP gene, (b) cDNA comprising the nucleotide sequence presented in SEQ ID NO:1 or comprising the nucleotide sequence presented in SEQ ID NO:14, (c) DNA capable of hybridization to a DNA of (a) or (b) under moderately stringent conditions and which encodes a biologically active ADMP, and (d) DNA which is degenerate as a result of the genetic code to a DNA defined in (a), (b) or (c) and which encodes a biologically active ADMP. ADMPs encoded by such DNA equivalent sequences are encompassed by the invention.

DNAs that are equivalents to the DNA sequence of SEQ ID NO:1 will hybridize under moderately stringent or highly stringent conditions to the double-stranded native DNA sequence that encode polypeptides comprising amino acid sequences of 1 to Xaa of SEQ ID NO:2, wherein Xaa is an amino acid from 431–837. DNAs that are equivalents to the DNA sequence of SEQ ID NO:14 will hybridize under moderately stringent or highly stringent conditions to the double-stranded native DNA sequence that encode polypeptides comprising amino acid sequences of 1 to Xaa of SEQ ID NO:15, wherein Xaa is an amino acid from 479–930. Examples of ADMP proteins encoded by such DNA, include, but are not limited to, ADMP fragments and ADMPs comprising inactivated N-glycosylation site(s), inactivated KEX2 protease processing site(s), or conservative amino acid substitution(s), as described above. ADMP proteins encoded by DNA derived from other species, wherein the DNA will hybridize under conditions of moderate or high stringency to the complement of the cDNA of SEQ ID NO:1 or the cDNA of SEQ ID NO:14 are also encompassed by this invention.

ADMP polypeptides may exist as oligomers, such as covalently-linked or non-covalently-linked dimers or trimers. Oligomers may be linked by disulfide bonds formed between cysteine residues on different aggrecanase polypeptides. In one embodiment of the invention, an ADMP dimer is created by fusing the ADMP to the Fc region of an antibody (e.g., IgGI) in a manner that does not interfere with biological activity of the ADMP. The Fc polypeptide preferably is fused to the C-terminus of a soluble ADMP. General preparation of fusion proteins comprising heterologous polypeptides fused to various portions of antibody-derived polypeptides (including the Fc domain) has been described, e.g., by Ashkenazi et al. (*PNAS USA* 88:10535, 1991) and Byrn et al. (*Nature* 344:677, 1990). A gene fusion encoding the ADMP:Fc fusion protein is inserted into an appropriate expression vector. ADMP:Fc fusion proteins are allowed to assemble much like antibody molecules, whereupon interchain disulfide bonds form between Fc polypeptides, yielding a divalent ADMP. If fusion proteins are made with both heavy and light chains of an antibody, it is possible to form an aggrecanase oligomer with as many as four aggrecanase molecules. Alternatively, one can link two soluble aggrecanase domains with a peptide linker.

Expression vectors containing a nucleic acid sequence encoding an ADMP can be utilized to produce recombinant protein. An ADMP DNA sequence can be operably linked to suitable transcriptional and translational regulatory nucleotide sequences using established procedures. Regulatory sequences, which are usually derived from viral, mammalian or insect genes, can include transcriptional promoters, operators, or enhancers, mRNA ribosomal binding sites, and/or other appropriate sequences which drive transcription, translation initiation and termination. When a regulatory sequence is functionally related to the ADMP DNA sequence, the nucleotide sequence is operably linked. Thus, a promoter nucleotide sequence is operably linked to an ADMP DNA sequence if the promoter nucleotide sequence drives the transcription of the ADMP DNA sequence. The expression vector may additionally include an origin of replication, to mediate replication in the desired host cells, as well as a selectable marker gene for the identification and selection of transformants or transfectants.

Expression vectors may also include signal peptide sequences (secretory leaders), which may be fused in-frame to the ADMP sequence. The inclusion of the signal sequence on the resultant fusion protein can enhance extracellular secretion of the ADMP polypeptide. The signal peptide may be cleaved from the ADMP protein upon export through the cellular secretory pathway.

Host cells for expression of ADMP proteins include prokaryotes and yeast or higher eukaryotic cells. Appropriate cloning and expression vectors for use with fungal, yeast, and mammalian cellular hosts are described for example, in Pouwels et al. *Cloning Vectors: A Laboratory Manual*, Elsevier, N.Y., (1985). In vitro translation systems could also be employed to produce ADMP polypeptides using RNAs derived from DNA constructs disclosed herein.

Prokaryotes include gram negative or gram positive organisms, for example, *E. coli* or Bacilli. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, an ADMP polypeptide may include an N-terminal methionine residue to facilitate expression of the recombinant polypeptide in the prokaryotic host cell. The N-terminal Met may be cleaved from the expressed recombinant ADMP polypeptide.

Prokaryotic expression vectors generally comprise one or more phenotypic selectable marker genes. Examples of phenotypic selectable marker genes include a gene encoding a protein that confers antibiotic resistance (amplicillin, tetracycline, kanamycin), or that supplies an autotrophic requirement (leucine). Examples of useful expression vectors for prokaryotic host cells include those derived from commercially available plasmids such as the cloning vector pBR322 (ATCC 37017). The cloning vector pBR322 contains genes for ampicillin and tetracycline resistance and thus provides simple means for identifying transformed cells. To construct an expression vector using pBR322, an appropriate promoter and an ADMP DNA sequence are inserted into the pBR322 vector. Other commercially available vectors include for example, pET (Novagen, Madison, Wis., USA) and PGEMI (Promega Biotec, Madison, Wis., USA).

Promoter sequences commonly used for recombinant prokaryotic host cell expression vectors include B-lactamase (penicillinase), lactose promoter system (Chang et al., *Nature* 275:615, 1978; and Goeddel et al., *Nature* 281:544, 1979), a phage 1 $P_L$ promoter, tryptophan (trp) promoter system (Goeddel et al., *Nucl. Acids Res.* 8:4057, 1980) and tac promoter (Maniatis, *Molecular Cloning: A Laboratory Mammal*, Cold Spring Harbor Laboratory, p. 412, 1982).

ADMP polypeptides alternatively may be expressed in yeast host cells, preferably from the *Saccharomyces* genus (e.g., *S. cerevisiae*). Other genera of yeast, such as *Pichia K.*

*lactis* or *Kluyveromyces*, may also be employed. Yeast vectors will often contain an origin of replication sequence from a 2u yeast plasmid, an autonomously replicating sequence (ARS), a promoter region, sequences for polyadenylation, sequences for transcription termination, and a selectable marker gene. Suitable promoter sequences for yeast vectors include among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7,149, 1968; and Holland et al., *Blochem. L*7:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other appropriate vectors and promoters for use in yeast expression are described in Hiitzeman, EPA-73,657 or in Fleer et al., *Gene,* 107:285–195 (1991); and van den Berg et. al., *Bio/Technology,* 8:135–139 (1990). Another alternative is the glucoserepressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* (Ampr gene and origin of replication) into the above-described yeast vectors.

The yeast a-factor leader sequence, typically inserted between the promoter and the cDNA to be expressed, may be employed to mediate secretion of an ADMP polypeptide. See, e.g., Kurjan et al., *Cell* 3D:933, 1982; Bitter et al., and *Proc. Natl. Acad. SCI. USA* 11:53301, 1984. Other leader sequences suitable for facilitating secretion of recombinant polypeptides from yeast hosts are known to those skilled in the art. A leader sequence may be modified near its 3' end to contain one or more restriction sites. This will facilitate fusion of the leader sequence to the structural gene.

Yeast transformation protocols are known to those skilled in the art. One such protocol is described by Hinnen et al., *Proc. Natl. Acad. Sci. USA* 11:1929, 1978. The Hinnen et al. protocol selects for Trp+ transformants in a selective medium, wherein the selective medium consists of 0.67% yeast nitrogen base, 0.5% casamino acids, 2% glucose, 10 ug/ml adenine and 20 ug/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 ug/ml adenine and 80 ug/ml uracil. Derepression of the ADH2 promoter occurs when glucose is exhausted from the medium.

The expression of recombinant ADMP polypeptides can also be carried out in mammalian or insect host cell culture systems. Established cell lines of mammalian origin may also be employed. Examples of suitable mammalian host cell lines include L cells, C127 cells, 3T3 cells (ATCC CCL 163), the COS-7 line of monkey kidney cells (ATCC CRL 1651) (Gluzman et al., *Cell* 2.1:175, 1981), HeLa cells, Chinese hamster ovary (CHO) cells, and BHK (ATCC CRL 10) cell lines, and the CV-1/EBNA-1 cell line derived from the African green monkey kidney cell line CVI (ATCC CCL 70) as described by McMahan et al. (*EMBO J.* 10: 2821, 1991). Baculovirus systems for production of heterologous proteins in insect cells are reviewed by Luckow and Summers, *Bio/Technology* 6:47 20 (1988).

Generally, the expression of eukaryotic genes in mammalian host cells is driven by viral-genome-derived early and late promoters, enhancer, splice signals and polyadenylation sites, which are included in a variety of mammalian expression vectors. Viral early and late promoters are particularly useful because both are easily obtained from a viral genome as a fragment which may also contain a viral origin of replication (Fiers et al. *Nature* 273: 113, 1978). Typically used viral transcriptional and translational control sequences are derived from Rous sarcoma virus, Polyoma virus, Adenovirus 2, Simian Virus 40 (SV40), and human cytomegalovirus (CMV).

An isolated and purified ADMP protein according to the invention may be produced by recombinant expression systems as described above or purified from media of stimulated tissue or cells. ADMPs can be substantially purified, as indicated by a single protein band upon analysis by SDS-polyacrylamide gel electrophoresis (SDS-PAGE). One process for producing an ADMP consists of culturing a host cell transformed with an expression vector containing a DNA sequence that encodes an ADMP under conditions sufficient to promote expression of the ADMP. The ADMP is then recovered from culture medium or cell extracts, depending on the expression system used. As known to one skilled in the art, procedures for purifying a recombinant protein will vary according to such factors as the type of host cells used and whether or not the recombinant protein is secreted into the culture medium. For example, when expression systems that secrete the recombinant protein are employed, the culture medium first may be concentrated using a commercially available protein concentration filter, for example, an Amicon or Millipore, Pellicon ultrafiltration unit. Following the concentration step, the concentrate can be applied to a purification matrix such as a gel filtration medium, or an anion or a cation exchange resin of the type commonly used in protein purification. Finally, one or more reverse-phase high-performance liquid chromatography (RP-HPLC) steps utilizing hydrophobic RP-HPLC media can be employed to further purify the ADMP. Some or all of the foregoing purification steps, in various combinations, can be used to provide an isolated and purified recombinant protein.

In addition to recombinantly producing ADMPs, ADMPs may be isolated and purified from conditioned media of stimulated bovine nasal cartilage cultures, such stimulation effected with cytokines such as IL-1 or TNF, retinoic acid, adhesion molecule fragments such as fibronectin fragments or other stimuli. Other sources of aggrecanase may be used, including but not limited to, cartilage and other aggrecanase-expressing tissues from various species, and ADMPs may also be produced by stimulated cells in culture. ADMP probes containing nucleic acid sequences that hybridize to native ADMP nucleotide sequence, available through the invention, can be used to enable identification of cell lines, cells or tissue sources of ADMPs. Once a source of ADMPs is identified, ADMPs may be isolated and purified by optimally stimulating the source cells or tissue to produce ADMPs.

It is possible to utilize an affinity column comprising an ADMP-binding protein to affinity-purify expressed ADMP polypeptides. ADMP polypeptides can be removed from an affinity column using conventional techniques, e.g., in a high salt elution buffer and then dialyzed into a lower salt buffer for use or by changing pH or other components depending on the affinity matrix utilized. Example 5 describes a procedure for employing ADMPs of the invention to generate antibodies directed against the ADMPs.

Recombinant protein produced in bacterial culture is usually isolated by initial disruption of the host cells, centrifugation, extraction from cell pellets if an insoluble polypeptide, or from the supernatant fluid if a soluble polypeptide. This isolation is followed by one or more concentrating steps such as salting-out, ion exchange, affinity purification or size exclusion chromatography. RP-HPLC can be employed for final purification steps. Microbial cells can be disrupted by any convenient method including freeze-thaw cycling, sonication, mechanical disruption, or use of cell-lysing agents.

Transformed yeast host cells are preferably used to express an ADMP as a secreted polypeptide in order to simplify purification. Secreted recombinant polypeptide from a yeast host cell fermentation can be purified by methods analogous to those disclosed by Urdal et al. (*J. Chromatog.* 2k:171, 1984).

Antisense or sense oligonucleotides comprising a single-stranded nucleic acid sequence (either RNA or DNA) capable of binding to a target ADMP mRNA sequence (forming a duplex) or to the ADMP sequence in the double-stranded DNA helix (forming a triple helix) can be made according to the invention. Antisense or sense oligonucleotides, according to the present invention, comprise a fragment of the coding region of an ADMP cDNA. Such a fragment generally comprises at least about 14 nucleotides, preferably from about 14 to about 30 nucleotides. The ability to create an antisense or a sense oligonucleotide, based upon a cDNA sequence for a given protein is described in, for example, Stein and Cohen, *Cancer Res.* 48:2659, 1988 and van der Krol et al., *BioTechniques* 6:958, 1988.

Binding of antisense or sense oligonucleotides to target nucleic acid sequences results in the formation of complexes that block translation (RNA), or transcription (DNA) by one of several means, including enhanced degradation of the duplexes, premature termination of transcription or translation. Thus, the antisense oligonucleotides may be used to block expression of ADMP proteins. Antisense or sense oligonucleotides further comprise oligonucleotides having modified sugar-phosphodiester backbones (or other sugar linkages) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences. Other examples of sense or antisense oligonucleotides include those oligonucleotides which are covalently linked to organic moieties and other moieties that increases affinity of the oligonucleotide for a target nucleic acid sequence, such as poly-(L-lysine). Further still, intercalating agents and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, CaPO4-mediated DNA transfection, electroporation, or by using gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retrovirus vector containing the inserted sequence, either in vivo or ex vivo. Suitable retroviral vectors include, but are not limited to, the murine retrovirus M-MuLV, N2 (a retrovirus derived from M-MuLV), or the double copy vectors designated DCT5A, DCT5B and DCT5C.

Sense or antisense oligonucleotides also may be introduced into a cell containing the nucleotide sequence by formation of a conjugate with a ligand binding molecule. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex. The sense or antisense oligonucleotide-lipid complex is preferably dissociated within the cell by an endogenous lipase.

Detection of ADMP enzymatic activity in crude culture media from tissue or cell cultures or partially-purified or purified ADMP preparations can be achieved by incubating the ADMP-containing material with an aggrecan substrate and monitoring the production of aggrecan fragments generated by specific cleavage at the Glu373-Ala374 bond using a neoepitope antibody to either the new N-terminus, ARGSV, or the new C-terminus, NITEGE, formed by cleavage at this bond. The ARGSV neoepitope antibodies used encompass, but are not limited to, the BC-3 monoclonal antibody (Hughes, C. E., et al., Biochem. J. 306:799–804, 1995). As used herein, "aggrecan" refers to the aggregating proteoglycan, aggrecan, from human or animal cartilage, as the native aggrecan isolated from tissue, as recombinant full-length aggrecan or as a recombinant protein representing a portion of the aggrecan molecule. Within an aspect of the invention, an ADMP may be utilized to identify additional ADMP-sensitive sites thus enabling activity to also be detected by monitoring the production of fragments formed by cleavage at alternative ADMP-sensitive sites using neoepitope antibodies to the new C-terminus or to the new N-terminus generated by ADMP-specific cleavage at these sites. Alternative sites in the aggrecan core protein encompass, but are not limited to the E1545-G1546, E1714-G1715, E1819-A1820, or E1919-L1920 bond (numbering based on the human aggrecan-core protein sequence). These human aggrecan ADMP-senstitive cleavage sites are conserved in aggrecan from various animal species although the absolute numbering based on the sequence of the aggrecan core protein may vary from species to species. Conserved amino acid sequences in various species around conserved ADMP-sensitive sites are shown below.

| Human | NITEGE$^{373}$ | $^{374}$ARGSVILT | (SEQ ID NO:22) |
|---|---|---|---|
| Bovine | NITEGE | ARGSVILT | (SEQ ID NO:23) |
| Rat | NITEGE | ARGNVILT | (SEQ ID NO:24) |
| Mouse | NVTEGE | ALGSVILT | (SEQ ID NO:25) |
| Pig | NITEGE | ARGTVILT | (SEQ ID NO:26) |
| Sheep | NITEGE | ARGNVILT | (SEQ ID NO:27) |
| Chicken | NVTEEE | ARGSI | (SEQ ID NO:28) |
| Horse | NITEGE | ARGNVILT | (SEQ ID NO:29) |
| Human | ASTASELE$^{1545}$ | $^{1546}$GRGTIGIS | (SEQ ID NO:30) |
| Bovine | ATTAGELE | GRGTIDIS | (SEQ ID NO:31) |
| Mouse | ATTSSELE | GRGTIGIS | (SEQ ID NO:32) |
| Rat | ATTASELE | GRGTISVS | (SEQ ID NO:33) |
| Human | PTTFKEEE$^{1714}$ | $^{1715}$GLGSVELS | (SEQ ID NO:34) |
| Bovine | PTTFKEEE | GLGSVELS | (SEQ ID NO:35) |
| Rat | PTTFREEE | GLGSVELS | (SEQ ID NO:36) |
| Mouse | PTTFREEE | GLGSVELS | (SEQ ID NO:37) |
| Human | TQAPTAQE$^{1819}$ | $^{1820}$AGEGPSGI | (SEQ ID NO:38) |
| Bovine | TQAPTAQE | AGEGPSGI | (SEQ ID NO:39) |
| Rat | TLAPTAQE | AGEGPSSI | (SEQ ID NO:40) |
| Mouse | TQAPTAQE | AGEGPSGI | (SEQ ID NO:41) |

-continued

| | | | |
|---|---|---|---|
| Chicken | TQTSVAQE | VGEGPSGM | (SEQ ID NO:42) |
| Human | TEPTISQE[1919] | [1920]LGQRPPVT | (SEQ ID NO:43) |
| Bovine | TEPTVSQE | LGQRPPVT | (SEQ ID NO:44) |
| Rat | TEPTVSQE | LGHGPSMT | (SEQ ID NO:45) |
| Mouse | TEPTVSQE | LGHGPSMT | (SEQ ID NO:46) |
| Chicken | TRPTVSQE | LGGETAVT | (SEQ ID NO:47) |
| Dog | TEPTVSQE | LAQRPPVT | (SEQ ID NO:48) |

Thus, aggrecan from various animal species, including but not limited to, bovine, dog, pig, rat, mouse, sheep, horse and chicken may also be used as a substrate for detecting ADMP activity. Utilizing neoepitope antibodies allows detection of fragments formed specifically by ADMP-mediated cleavage even in the presence of other proteolytic activities that may be present in crude preparations.

As used herein, the cleavage site "E272-374A" refers to the ITEGE373 (SEQ ID NO:49)-374ARGS (SEQ ID NO:50) bond of human aggrecan as well as to the homologous aggrecanase-sensitive cleavage site in aggrecan from various animal species, the cleavage site "E1545-1546G" refers to the SELE1545 (SEQ ID NO:51)-1546GRGT (SEQ ID NO:52) bond of human aggrecan as well as to the homologous aggrecanase-sensitive cleavage site in aggrecan from various animal species, the cleavage site "E1714-1715G" refers to the KEEE1714 (SEQ ID NO:53)-1715GLGS (SEQ ID NO:54) bond of the human aggrecan as well as to the homologous aggrecanase-sensitive cleavage site in aggrecan from various animal species, the cleavage site "E1819-1820L" refers to the TAQE1819 (SEQ ID NO:55)-1820AGEG (SEQ ID NO:56) bond of human aggrecan as well as to the homologous aggrecanase-sensitive cleavage site in aggrecan from various animal species, the cleavage site "E1919-1920L" refers to the ISQE1919 (SEQ ID NO:57)-1920LGQR (SEQ ID NO:58) bond of human aggrecan as well as to the homologous aggrecanase-sensitive cleavage site in aggrecan from various animal species.

A purified ADMP may also be assayed using any of a variety of protease assays known in the art. In general, an ADMP can be assayed through the use of a peptide substrate that represents the natural cleavage site of aggrecan cleavage. For example, in order to detect the cleavage of a substrate by an ADMP, the substrate can be tagged with a fluorescent group on one side of the cleavage site and with a fluorescence-quenching group on the opposite side of the cleavage site. Upon cleavage by the ADMP, quenching is eliminated thus providing a detectable signal. Alternatively, the substrate may be tagged with a calorimetric leaving group that more strongly absorbs upon cleavage. Alternatively, the substrate may have a thioester group synthesized into the cleavage site of the substrate so that upon cleavage by an ADMP, the thiol group remains and can be easily detected using conventional methods.

Within an aspect of the invention, an ADMP and peptides based on the amino acid sequence of the ADMP, may be utilized to prepare antibodies that specifically bind to the ADMP. Specific examples of such antibody preparation is described in Example 5 and 6 herein. The term "antibodies" is meant to include polyconal antibodies, monoclonal antibodies, fragments thereof such as F(ab')2, and Fab, as well as any recombinantly produced binding parameters. Antibodies are defined to be specifically binding if they bind an ADMP with a Ka of greater than or equal to about $1\times10^{-7}$ M. Affinities of binding partners or antibodies can be readily determined using conventional techniques, for example those described by Scatchard et al., *Ann. N.Y. Acad. Sci.*, 51:660 (1949).

Using standard procedures, polyclonal antibodies can be readily generated from a variety of sources such as horses, cows, goats, sheep, dogs, chickens, rabbits, mice or rats. In general a purified ADMP, or a peptide based on the amino acid sequence of the ADMP, that is appropriately conjugated is administered to the host animal typically through parenteral injection. The immunogenicity of the ADMP may be enhanced by the use of an adjuvant such as Freund's complete or incomplete adjuvant. Following booster immunizations, small samples of serum are collected and tested for reactivity to the ADMP or the ADMP peptides. Examples of various assays useful for such determination include those described in: *Antibodies: A Laboratory Manual*, Harlow and Lane (eds.), Cold Spring Harbor Laboratory Press, 1988; as well as procedures such as countercurrent immuno-electrophoresis (CIEP), radioimmunoassay radio-immunoprecipitation, enzyme-linked immuno-sorbent assays (ELISA), dot-blot assays, and sandwich assays.

Monoclonal antibodies can be readily prepared using standard procedures such as those described in Monoclonal Antibodies, Hybridomas: *A New Dimension in Biological Analyses*, Plenum Press, Kennett, McKearn, and Bechtol (eds.), 1980. The host animals, for example mice, are injected intraperitoneally at least once, and preferably at least twice at approximate 3 week intervals, with an isolated and purified ADMP or conjugated ADMP peptide, optionally in the presence of adjuvant. Mouse sera are then assayed by the conventional dot-blot technique or antibody-capture technique, to determine which animal is best to use in the production of hybrid cells. Approximately two to three weeks later, the mice are given an intravenous boost of the ADMP or conjugated ADMP peptide. Mice are subsequently sacrificed and using established protocols, the spleen cells are fused with commercially available myeloma cells. The fusing agent can be any suitable agent used in the art, for example, polyethylene glycol. The fused cells are spread onto plates containing media that allows for their selective growth. The fused cells are grown for approximately eight days. Supernatant from the resulting hybridomas is collected and added to a plate that has been coated with goat anti-mouse Ig. Following washes, a label, such as $I^{125}$-ADMP, is added to each well and followed by incubation. Positive wells are subsequently detected by autoradiography. Positive clones can be grown in bulk culture and the supernatant subsequently purified utilizing a Protein A column.

Other types of "antibodies" may be produced using the information provided herein in conjunction with the state of knowledge in the art. Humanized antibodies that are capable of specifically binding ADMPs are also encompassed by the instant invention.

Once isolated and purified, the antibodies against ADMPs can be used to detect the presence of ADMPs in a sample using established assay protocols. The antibodies of the invention can also be used therapeutically to bind to an ADMP and inhibit its activity in vivo.

The purified ADMPs according to the invention will facilitate the discovery of inhibitors of aggrecanases, and thus, inhibitors of cartilage aggrecan degradation. The use of a purified ADMP polypeptide in the screening of potential inhibitors thereof is important and can virtually eliminate the possibility of interfering reactions with contaminants. Such a screening assay for detecting the aggrecanase-inhibiting activity of a molecule would typically involve mixing the potential inhibitor molecule with an appropriate substrate, incubating an ADMP that is at least substantially purified with the mixture, and determining the extent of substrate cleavage. While various appropriate substrates may be designed for use in the assay, preferably the native aggrecan monomer or a peptidyl substrate which encompasses the $E^{374}$-$^{374}A$ cleavage site within the interglobular domain of the aggrecan core protein.

Alternatively, monitoring cleavage at aggrecanase-sensitive sites within the C-terminus of the aggrecan core protein, including $E^{1545}$-$^{1546}G$, $E^{1714}$-$^{1715}G$, $E^{1819}$-$^{1820}A$, $E^{1919}$-$^{1920}L$ (numbering based on human aggrecan-core protein), can be used for detecting aggrecanase-inhibiting activity of a molecule by employing appropriate peptidyl substrates or the native aggrecan monomer and neoepitope antibodies.

In addition, ADMP polypeptides can be used for structure-based design of aggrecanase-inhibitors. Such structure-based design is also known as "rational drug design." The ADMP polypeptides can be three-dimensionally analyzed by X-ray crystallography, nuclear magnetic resonance or homology modeling. The use of ADMP structural information in molecular modeling software systems to assist in the inhibitor design and inhibitor-ADMP interaction is also encompassed by the instant invention. Such computer-assisted modeling and drug design can utilize information such as chemical conformational analysis, electrostatic potential of the molecules, and protein folding. A particular method of the invention comprises analyzing the three-dimensional structure of ADMPs for likely binding sites of substrates, synthesizing a new molecule incorporating a predictive reactive site, and assaying the new molecule as described above.

The following examples provide an illustration of embodiments of the invention and should not be construed to limit the scope of the invention which is set forth in the appended claims. In the following examples, all methods described are conventional unless otherwise specified.

EXAMPLE 1

Purification of ADMP-1

This example describes a method for purifying ADMP-1. ADMP-1 was isolated and purified from the conditioned media of stimulated bovine nasal cartilage. Thirty liters of conditioned media, from approximately 1000 grams of bovine nasal cartilage, was generated by stimulating with interleukin-1β (IL-1). In order to accumulate ADMPs in culture media, cartilage matrix was first degraded and depleted of endogenous aggrecan by stimulation with 500 ng/ml human recombinant IL-1 for 6 days with media changes every 2 days. Cartilage was then stimulated for an additional 10 days with 500 ng/ml IL-1 to generate accumulation of soluble, active ADMPs in the media. By replacing the media and restimulating the cartilage with IL-1 every other day during the accumulation phase, approximately 5 times more aggrecanase activity was generated than by allowing accumulation of ADMPs in conditioned media without media change. Media, containing the ADMPs, was frozen at –70° C. for subsequent purification.

All purification steps were performed at 4° C. unless otherwise specified. Five liters of frozen conditioned media was thawed overnight and supplemented with 1 μM leupeptin, 1 μM pepstatin, 1 mM PMSF (PMSF is phenylmethylsulfonyl-fluoride), and 0.05% Brij-35. This was clarified by passage through a 1.2 micron Gelman Capsule filter, and loaded onto a 20×10 cm Macro S support column at a flow rate of 40 ml/min. The column was washed with Buffer A (Buffer A contains 50 mM HEPES (HEPES is N-(2-hydroxyethyl) piperazine-N'-(2-ethanesulfonic acid), pH 7.5, 10 mM $CaCl_2$, 100 mM NaCl, 0.05% (v/v) Brij-35) until the absorbance at 280 nm returned to the pre-load baseline value. ADMPs were eluted from the column with 750 ml of buffer A containing 1.0 M NaCl.

ADMPs were detected at this point by their ability to cleave purified bovine aggrecan monomers isolated from bovine nasal cartilage by the following procedure: Aggrecan was extracted from the cartilage by stirring at 4° C. for 48 hours in 10 volumes of 4M guanidine-HCl in 0.05 M sodium acetate, pH 5.8, containing the protease inhibitors, 0.01M EDTA (EDTA is ethylenediaminetetraacetic acid), 0.1M 6-aminohexanoic acid, 2 mM PMSF and 0.05M benzamidine HCl. Aggrecan monomers were isolated by equilibrium density gradient centrifugation in cesium chloride [Hascall, V. C. and Sajdera, S. W. (1969) J. Biol. Chem. 244, 2384–2396.] and the bottom of this gradient (d>1.54 g/ml) containing the aggrecan monomers, was dialyzed at 4° C. against water and lyophilized.

These aggrecan monomers (500 nM) were incubated at 37° C. for at least 4 hr with ADMPs eluted from the Macro S support column in a final volume of 200 ul in Buffer B (Buffer B contains 50 nM Tris, pH 7.6, containing 0.1 M NaCl and 10 mM CaCl2), quenched with 20 mM EDTA and analyzed for aggrecan fragments produced exclusively by cleavage at the $Glu^{373}$-$Ala^{374}$ bond within the aggrecan core protein using the monoclonal antibody, BC-3 (Hughes, C. E., et al., Biochem. J. 306:799–804, 1995). This antibody recognizes aggrecan fragments with the N-terminal sequence $A^{374}RGSVIL$ . . . (SEQ ID NO:59), generated upon cleavage by ADMPs. The BC-3 antibody recognizes this neoepitope only when it is in the N-terminus and not when it is present internally within aggrecan fragments or within the intact aggrecan core protein. Other proteases produced by cartilage in response to stimulation of chondrocytes do not cleave at the $Glu^{373}$-$Ala^{374}$ site, therefore only products produced upon cleavage by ADMPs are detected.

Removal of the glycosaminoglycan (GAG) side chains from aggrecan is necessary for the BC-3 antibody to recognize the ARGSVIL epitope of the core protein. Therefore, to remove GAGs from the aggrecan, samples were were enzymatically deglycosylated with chondroitinase ABC (#EC4.2.2.4; Seikaguku Co., Kogyo, Japan) 0.1 units/10 ug GAG in Buffer D (Buffer D contains 50 mM sodium acetate, pH 6.5, 100 mM NaCl) for 2 hr at 37° C. and then with keratanase(#EC3.2.1.103; Seikaguku Co., Kogyo, Japan) (0.1 units/10 ug GAG) and keratanase II (Seikaguku Co., Kogyo, Japan) (0.002 units/10 ug GAG) in Buffer D for 2 hr at 37° C.

After digestion, the samples were precipitated with 5 volumes of acetone and reconstituted in an appropriate volume of SDS-PAGE sample buffer, loaded on 4–12% gradient gels and then separated by SDS-PAGE under non reducing conditions, transferred overnight to nitrocellulose and immunolocated with 1:1000 dilution of the monoclonal antibody BC-3. Subsequently, membranes were incubated with goat anti-mouse IgG alkaline phosphatase conjugate and aggrecan catabolites visualized by incubation with the appropriate substrate (#S3721; Promega Western blot alkaline phosphatase system) for 10–30 min to achieve optimal color development. BC-3-reactive aggrecan fragments were then quantified by scanning densitometry.

The material that eluted from the Macro S support column with 0.1 M NaCl had about a 20-fold higher specific activity than the starting material. The eluted material was supplemented with Compound A (N-3-methyl-(3R)-2-[(2S)-2-[(1R)-2-(hydroxyamino)-1-methyl-2-oxoethyl]-4-methylpentanoyl]hexahydro-3-pyridazinecarboxamide), a hydroxamic acid-based broad spectrum inhibitor of matrix metalloproteinases that is ineffective as an inhibitor of ADMP activity. The sample was then loaded onto a 10×7.5 cm gelatin-agarose column at a flow rate of 0.5 ml/min. Compound A was added to prevent degradation of the gelatin column by matrix metalloproteinases present during this purification step. Material passing through this column contained the ADMP activity and was collected and concentrated 6 to 7-fold using an Amicon Diaflo pressure concentrator fitted with a YM-30 membrane.

ADMP activity is inhibited by both tissue inhibitor of metalloproteinases-1 (TIMP-1) and by a number of hydroxamic acid-based inhibitors of matrix metalloproteinases. Therefore TIMP-1 and a hydroxamate inhibitor of aggrecanase activity were used to further affinity purify ADMP. Compound A was included during the affinity purification to prevent matrix metalloproteinases present in the material from binding to the TIMP-1 or to the hydroxamate inhibitor of ADMP.

The concentrated material from the gelatin-agarose column containing the ADMP activity was incubated with 1 uM bovine TIMP-1 in the presence of 1 uM Compound A in for at least 30 minutes to allow ADMP to bind to the TIMP-1. The TIMP-1 was subsequently complexed by incubating with a TIMP-1 monoclonal antibody at a 1:5000 dilution for at least 30 minutes. The TIMP-1-antibody complex was then applied to a 10 ml protein A column. The column was washed 3× with Buffer E (Buffer E contains 10 mM Tris, pH 7.5, 250 mM NaCl, 0.025% Tween20) and the protein was eluted from the column with 100 mM glycine/HCl, pH 2.5.

An ADMP-inhibitor hydroxamate affinity resin was produced in the following manner. POROS 20-NH perfusive chromatographic media (Perseptive Biosystems), a highly crosslinked poly(styrene divinylbenzene) polymer, was mixed overnight with four equivalents of Fmoc-beta-alanine, four equivalents HBTU (O-Benzotriazole-N,N,N',N'-tetramethyl-uronium hexafluorophosphate), and eight equivalents DIEA (N,N diisopropylethylamine) in DMF (dimethylformamide). The resin was rinsed several times with DMF, then the FMOC group was removed with 20% piperidine/DMF. This coupling/deprotecting scheme was repeated three more times, resulting in four beta-alanine residues coupled to the resin. After the final piperidine deprotection, 1.5 equivalents of a t-butyl protected hydroxamic acid capable of inhibiting ADMP activity was coupled with 1.5 equivalents HBTU and 3 equivalents DIEA in DMF. After rinsing with DMF and $CH_2Cl_2$, the t-butyl group was removed by mixing overnight with TFA (trifluoroacetic acid), leaving the hydroxamic acid. The resin was thoroughly rinsed with $CH_2Cl_2$ and dried under vacuum.

The eluate from the protein A column was neutralized with 1 M Tris base to pH 7.5 and then incubated for 2 hours with the aggrecanase-inhibitor hydroxamate resin at a ratio of 1 mg resin for every 1 ml of eluate. Following the incubation, the resin was spun down and washed at 4° C. with Buffer E, three times, 10 minutes each wash. Bound ADMP was eluted from the resin by mixing with approximately 0.5–1.0 ml 4 M GuHCl for 30 minutes at room temperature. The eluate, containing the ADMP activity, was dialyzed against Buffer F (Buffer F comprises 50 mM Tris, pH 7.6, 100 mM NaCl, 5 mM $CaCl_2$) for 48 hours at 4° C. A portion of the eluate was run on a SDS-PAGE gel (10–20%), and silver staining revealed one predominant protein, ADMP-1, that ran as a doublet between the 64 and 92 kDa markers on the gel at approximately 67 kDa.

Incubation of the GuHCl-eluted ADMP-1 with isolated bovine aggrecan produced a pattern of BC-3-reactive fragments similar to that produced upon cleavage of cartilage aggrecan by endogenous aggrecanase in bovine nasal cartilage stimulated with IL-1.

Binding of this 67 kDa ADMP-1 doublet to the aggrecanase-inhibitor hydroxamate resin was blocked by inclusion during affinity purification of 10 uM Compound B ((2S, 11S, 12S)-12-isobutyl-2-[(methylamino)carbonyl]-11 [(hydroxylamino)carbonyl]-8,13-dioxo-1,7-diazacyclotridecane), a potent ADMP inhibitor. Thus, the binding of the 67 kDa ADMP-1 to the affinity resin was not affected by the presence of Compound A (a potent inhibitor of matrix metalloproteinases that is inactive in inhibiting ADMPs), but was blocked by Compound B (a potent ADMP inhibitor).

A region of the SDS-PAGE gel containing the 67 kDa ADMP-1 protein was excised along with a control region of the same gel which did not contain any detectable protein. Gel slices were incubated with 1% Triton X-100 for 1 hour at room temperature to remove the SDS for the gel. The gel was then crushed in 1 ml final volume of Buffer G (Buffer G contains 50 mM Tris, pH 7.5, 100 mM NaCl, 10 mM $CaCl_2$) and dialyzed in 10 kDa cutoff dialysis membrane for 48 hours against 12 liters of Buffer B at 4° C. ADMP activity was then determined by incubation with aggrecan substrate and monitoring products using the BC-3 antibody. The region of the gel containing the 67 kDa ADMP-1 protein exhibited activity while that of the control portion of the gel did not.

Generation of Peptides and Sequencing

The two protein bands running as a doublet at approximately 67 kDa and identified with ADMP activity by elution from SDS gels, were immobilized on PVDF and subjected to N-terminal amino acid sequence analysis as follows. The N-terminal sequence analyses were performed using the Hewlett-Packard G1005A N-terminal sequencer [Miller, C. G. (1994) Methods: A Companion to Methods in Enzymology 6, 315–333]. These analyses of PVDF-bloted protein were carried out using a modification of the Hewlett-Packard Routine 3.0 Sequencing Methods [Hewlettt-Packard technical note TNF95-1: Routine 3.0 Sequencing Methods] in combination with the Hewlett-Packard PTH 4.M HPLC Method [Hewlett-Packard technical note TN95-6: PTH 4.M HPLC Method]. The modifications of the sequencing methods involved: (1) the replacement of the lower SAX sample column with a lower RP adapter column and (2) the substitution of a mixture of LC-A buffer and water (LC-A: water; 2:1) for solvent S4 at the step where the PTH-amino acids were resuspended for injection into the HPLC. All sequencer reagents were from Hewlett-Packard and the HPLC-grade water used to dilute the LC-A as described above was from Aldrich Chemical Company.

Both bands of the 67 kDa doublet represented the same protein and the sequence of the first 27 residues were determined to be:

SEQ ID NO:4 FASLSRFVETLVVADDKMAAFHGAGLK

Two internal fragments, a 7-mer and a 11-mer, from a tryptic digestion of the 67 kDa ADMP-1 protein were sequenced and have the following sequences:

SEQ ID NO:5 YTGVAPR

SEQ ID NO:6 ALGYYYVLDP

EXAMPLE 2

Purification of ADMP-2

This example describes a method for purifying a second member of the ADMP family, ADMP-2. The concentrated material from the gelatin-agarose column containing the ADMP activity prepared as detailed in Example 1 was loaded onto a 3×20 cm phenyl-sepharose column that had been equilibrated with buffer A containing 10% (w/v) ammonium sulfate and without the Brij-35 detergent. The column was then washed with 150 ml of equilibration buffer. Proteins were eluted with a 400 ml gradient from 10% to 0% ammonium sulfate in equilibration buffer at a flow rate of 2 ml/min. At the end of the gradient phase, proteins were further eluted from the column with an additional 200 ml of 0% ammonium sulfate equilibration buffer. Fractions were collected throughout the loading, washing and elution phases and analyzed for ADMP activity. Fractions containing ADMP activity were pooled.

Material that eluted from the phenyl sepharose column with ammonium sulfate had about 87-fold higher specific activity than the starting material. These pooled fractions were loaded onto a 4×60 cm CM column that had been equilibrated with buffer H (buffer H contains 50 mM HEPES, 0.1 M NaCl, pH 7.5). The column was washed with 150 ml of buffer H, and then proteins were eluted from the column with a 300 ml gradient from 0.1 to 1.0 M NaCl in buffer H at a flow rate of 1.5 ml/min. Fractions were collected throughout the loading, washing, and elution phases and analyzed for ADMP activity. Fractions with high enzymatic activity were pooled. While still containing contaminating proteins, the enzyme at this stage was of adequate purity for use in high throughput screens designed to find small molecular weight inhibitors of ADMP activity.

The pooled fractions from the CM column containing ADMP activity had about a 500 fold higher specific activity than the starting material. This material was concentrated approximately 10-fold with an Amicon Diaflo pressure concentrater fitted with a YM-30 membrane. Samples of 2 ml of the concentrate were then applied to a 2×200 cm Sephacryl S-200 column equilibrated with Buffer H. The column was eluted isocratically in the same buffer at a flow rate of 0.2 ml/min. Fractions of 4 ml were collected throughout the elution and analyzed for ADMP activity. Pooled fractions containing ADMP activity had about a 3500-fold higher specific activity than the starting material.

The ADMP eluted from the sizing column was concentrated as described above to a final volume of 1 ml and injected onto a (30 mm×4.6 mm) $C_4$ alkylsilane-derivatized silica column and eluted with a linear gradient from 0 to 50% (v/v) acetonitrile in 0.1% aqueous TFA, at a flow rate of 1 ml/min. Fractions were collected throughout the elution phase, and immediately diluted 10-fold with Buffer A. As long as the acetonitrile concentration was diluted quickly, good recovery of enzymatic activity was observed from this column. Pooled fractions containing ADMP activity had about 100,000-fold higher specific activity than the starting material.

Analysis of the HPLC purified ADMP by SDS-PAGE with silver staining demonstrated the presence of multiple protein bands ranging in apparent molecular weights from approximately 90 to 30 kDa. Prominent bands were observed in the range of 65 to 40 kDa. To identify which protein band(s) corresponded to the ADMP activity, two samples of the HPLC purified ADMP were electrophoretically fractionated in adjacent wells of a 10% Tris-glycine polyacrylamide gel under non-reducing conditions. One lane was stained with silver. The other lane was cut horizontally into 22 approximately equal volume slices, each representing a different molecular weight range. The individual slices were crushed and soaked in 100 µl of 20 mM Tris, 10 mM $CaCl_2$ 100 mM NaCl, 2.5% Triton-X100. The samples were incubated in this buffer at 4° C. overnight to renature the enzyme and elute it from the gel slice into the supernatant solution. The resulting solutions were tested for ADMP activity. ADMP activity was associated with four protein bands, centered at ca. 64, 62, 54 and 50 kDa.

Generation of Peptides and Sequencing

The four protein bands identified with ADMP activity by elution from SDS gels were immobilized on PVDF and subjected to N-terminal amino acid sequence analysis. The 64 kDa protein yielded 41 cycles of sequence having the following composition:

SEQ ID NO:16 SISRARQVEL LLVADASMAR MYGR- GLQHYL LTLASIANKLYF

The 62, 54, and 50 kDa protein bands yielded the same N-terminal amino acid sequence as found in the 64 kDa band.

Based on these results it appeared that the 64, 62, 54 and 50 kDa protein bands displaying ADMP activity represent different forms of the same ADMP-2 protein. The difference in molecular weights of these four bands is most likely the result of differential processing of the four forms (e.g., differential glycosylation or C-terminal proteolytic processing).

EXAMPLE 3

Cloning of Human ADMP-1

This example describes a procedure for isolating a DNA sequence encoding human ADMP-1. N-terminal sequence obtained from the 67-kDa protein was shown to be 62% identical to the murine ADAMTS-1 protein (K. Kuno, et al. J. Biol. Chem. 272:556–562, 1997), suggesting that the 67 kDa protein was a member of the ADAM family of proteins. As defined herein and in the reference above, the name "ADAMTS-1" is an abbreviation for A disintegrin and metalloproteinase with thrombospondin motifs. Upon subsequent internal peptide sequencing, SEQ ID NO:6 was shown to be 50% identical to ADAMTS-1 and 91% (10/11) identical to sequences encoded by a murine EST 474985 (Accession number AA041973). Based on the high degree of identity between the latter internal peptide sequence and sequences encoded by EST474985, we proceeded to clone the human sequences representing the human homologue of murine EST 474985.

Two approaches were utilized in the cloning of the human homologue of murine EST 474985. In the first, the cDNA from which EST474985 was obtained was sequenced in its entirety, with the resulting sequence being used to search the EST data base for human ESTs with significant homology. In the second approach, human sequences were amplified using PCR primers designed from murine EST 474985 (SEQ ID NO:7 and SEQ ID NO:8). Both approaches provided us with sequence from the human homologue. A human EST (Accession number D45652) was identified that contained sequences having significant homology to the 1.7 kb murine cDNA from which EST 474985 was derived. The level of identity was 80% overall at the nucleotide level and contained sequences from the non-coding 3' untranslated region. Utilizing the second approach, we were able to obtain a 190 bp amplicon from human heart cDNA. Subsequent DNA sequence analysis indicated that the human PCR product was 89% identical at the nucleotide level to the murine EST, with the deduced peptide sequences being 96% identical.

We were successful at obtaining additional coding sequences utilizing PCR primers designed from the human EST and the 190 bp PCR product. A 2-kb clone was obtained using sense and anti-sense primers designed from the 190-bp PCR product (SEQ ID NO:9) and the human 3' EST (SEQ ID NO:10), respectively. Utilizing antisense primers designed from the 190-bp PCR product (SEQ ID NO:11 and SEQ ID NO:12), we were able to clone a 2.2-kb 5' RACE (rapid amplification of cDNA ends) product. Six clones from the 5' and 3' PCRs were sequenced in order to obtain a consensus sequence for the cDNA. A total 4.2-kb of sequence has been assembled (SEQ ID NO:1). The assembled cDNA contains a 2511-bp open reading frame encoding 837 amino acids (SEQ ID NO:2) with multiple in-frame stop codons being present upstream of the start methionine. The cDNA encodes sequences present in the N-terminal peptide sequence (SEQ ID NO:4), with the cDNA containing all 27 residues seen in the N-terminal sequence of the 67 kDa ADMP-1 protein. The N-terminus of the isolated 67 kDa ADMP-1 begins with amino acid 213 of SEQ ID NO:2, indicating that this protein lacks the propeptide domain of the molecule. The cDNA also encodes sequences present in the internal peptide sequences (SEQ ID NO:5 and SEQ ID NO:6), with sequences encoded by the cDNA being identical in six of seven positions for the first peptide and ten of eleven positions for the second peptide. The deduced protein sequence has homology to the previously reported ADAMTS-1 protein. Like ADAMTS-1, the ADMP-1 cDNA contains a propeptide domain, metalloproteinase domain and disintigrin-like domain. A noteworthy difference between the ADAMTS-1 and sequences encoded by the ADMP-1 cDNA is the presence of a single thrombospondin-domain in the deduced aggrecan degrading metallo protease, in contrast to the three thrombospondin domains seen in ADAMTS-1.

EXAMPLE 4

Cloning of ADMP-2

This example describes a procedure for isolating a DNA sequence encoding human ADMP-2. A closely related family member was identified by using the deduced ADMP-1 peptide sequence to search the EST data base. Sequences encoded by murine EST 569515 were shown to be 67% identical to sequences encoded by the ADMP-1 cDNA sequence. Further sequence analysis of the murine cDNA from which the EST 569515 was obtained indicated that it encoded sequences that were 95% (39/41) identical and 100% similar to the N-terminal sequence of the purified 50/64 kD aggrecanase, ADMP-2. These data indicated that the murine cDNA encodes the ADMP-2. PCR primers (SEQ ID NO: 17 and SEQ ID NO: 18) were designed from the murine sequence and were used to amplify a product from human heart cDNA, with the resulting product being 92% identical (150/163) at the nucleotide and 100% identical at the amino acid level to the murine sequences. Sequences present in the human amplicon were used to design a PCR primer for use in 3' RACE (SEQ ID NO: 19). However, only a partial 3' RACE clones was obtained using this approach. In order to obtain additional sequences, a human liver cDNA library was screened by PCR as described (D. I. Israel (1993) Nuc. Acids Res. 21, 2627–2631) using PCR primers designed from the human amplicon and the partial 3' RACE clone (SEQ ID NO: 19 and SEQ ID NO: 20). Two cDNA clones were obtained from the liver library, with each clone being approximately 5.5 kb is size.

Sequence analysis of the cDNA clones indicated that both cDNAs contain a 2793 bp open reading frame (SEQ ID NO: 14) encoding a 930 amino acid protein (SEQ ID NO: 15). The deduced protein sequence contains sequences that are 97.5% (40/41) identical and 100% similar to the bovine N-terminal peptide sequence of ADMP-2. The predicted protein encodes an ADMP family member closely related to human ADMP-1 and to the murine ADAMTS-1. All three proteins contain metalloproteinase-domains, disintigrin-like domains and thrombospondin motifs. These three family members were found to have a variable number of thrombospondin-submotifs. Murine ADAMTS-1 has been shown to contains two thrombospondin-submotifs (Kuno et al (1997) J. Biol;. Chem 272, 556–562), while the ADMP-2 cDNA encodes one thrombospondin-submotif and the ADMP-1 lacks the thrombospondin-submotifs altogether. Overall, the pro-domains of the three proteins are the least conserved, with the percent identity ranging from 15% for the ADMP-1 and ADMP-2 to 33% for mADAMTS-1 and ADMP-1. Greatest conservation was seen in the catalytic domains with the percent identity ranging from 48% (ADMP-1 and ADMP-2) to 62% (mADAMTS-1 and ADMP-1).

EXAMPLE 5

Preparation of Antibodies Against ADMP-1

This example describes a method for generating antibodies against ADMP-1. A peptide based on the N-terminus of the purified 67 kDa ADMP-1 was synthesized with the following sequence:

SEQ ID NO:13 CASLSRFVETLVVADDK

The peptide was linked to the carrier protein, keyhole limpet hemocyanin, and then subsequently used for immunization of a sheep. The coupled peptide antigen was suspended in PBS (phosphate-buffered saline) at 1 mg/ml with an equal volume of complete Freund's adjuvant. The material was mixed until it formed an emulsion, and then the material was injected at 6–8 subcutaneous sites. A total of 150–200 ug of coupled peptide was injected into the animal. The sheep was boosted every two weeks (for a total of five times) and a production bleed was collected at each time point. The affinity of the antibody was tested both in an ELISA and Western assay using the above antigen peptide conjugated to BSA. The polyclonal antiserum was positive for recognizing the BSA coupled peptide both in the ELISA and Western assays. The polyclonal sera was affinity purified over an antigen peptide (CASLSRFVETLWADDK, SEQ ID NO:60) column to capture the high affinity IgG antibodies and remove the low affinity antibodies.

EXAMPLE 6

Preparation of Antibodies Against ADMP-2

This example describes a method for generating antibodies against ADMP-2. A peptide based on the N-terminus of the purified 50/64 kDa ADMP-2 was synthesized with the following sequence:

SEQ ID NO: 21: SISRARQVELLAhxC-amide

Aminohexanoic acid (Ahx) was added to lengthen the peptide. The peptide was linked to the carrier protein, keyhole limpet hemocyanin, and then subsequently used for immunization of two rabbits. Five immunizations and bleedings yielded 200–250 ml of serum. The affinity of the antibody was compared with preimmune sera using an enzyme linked immunosorbent assay (ELISA) with BSA-coupled peptide on the solid phase. For all sera, results were expressed as the reciprocal of the serum dilution that resulted in an OD405 of 0.2 by detection with alkaline phosphatase-anti-rabbit IgG conjugate and NPP dye. The polyclonal antiserum was positive for recognizing the BSA coupled peptide in the ELISA and 90% of the aggrecanase activity in a 41-mer peptide-based enzymatic assay could be immunoprecipited by the antibody. The polyclonal sera was affinity purified over an antigen peptide column to capture the high affinity IgG antibodies and remove the low affinity antibodies. The resulting affinity-purified antibody works well for recognizing ADMP-2 bands in Western analysis.

What is claimed is:

1. An antibody that specifically binds to an ADMP capable of cleaving the $Glu^{373}$-$Ala^{374}$ peptide bond of an aggrecan core protein, wherein said ADMP comprises amino acids 1–837 of SEQ ID NO:2 and consists of the following domains from the N-terminus to the C-terminus; 1) a propeptide domain containing a furin cleavage site, followed by 2) a metalloprotease domain, followed by 3) a disintegrin-like domain, and 4) a thrombospondin homologous domain.

2. The antibody of claim 1 which is a monoclonal antibody.

3. A method of detecting the presence of an ADMP in a biological sample which comprises contacting the sample with an antibody of claim 1.

* * * * *

SEQUENCE LISTING

<160> NUMBER OF SEQ ID NOS: 60

<210> SEQ ID NO 1
<211> LENGTH: 4192
<212> TYPE: DNA
<213> ORGANISM: Homo sapiens

<400> SEQUENCE: 1

```
acagacacat atgcacgaga gagacagagg aggaaagaga cagagacaaa ggcacagcgg      60
aagaaggcag agacagggca ggcacagaag cggcccagac agagtcctac agagggagag     120
gccagagaag ctgcagaaga cacaggcagg gagagacaaa gatccaggaa aggagggctc     180
aggaggagag tttggagaag ccagacccct gggcacctct cccaagccca aggactaagt     240
tttctccatt tcctttaacg gtcctcagcc cttctgaaaa ctttgcctct gaccttggca     300
ggagtccaag cccccaggct acagagagga gctttccaaa gctagggtgt ggaggacttg     360
gtgccctaga cggcctcagt ccctcccagc tgcagtacca gtgccatgtc ccagacaggc     420
tcgcatcccg ggaggggctt ggcagggcgc tggctgtggg gagcccaacc ctgcctcctg     480
ctccccattg tgccgctctc ctggctggtg tggctgcttc tgctactgct ggcctctctc     540
ctgccctcag cccggctggc cagccccctc ccccgggagg aggagatcgt gtttccagag     600
aagctcaacg gcagcgtcct gcctggctcg ggcgcccctg ccaggctgtt gtgccgcttg     660
caggcctttg gggagacgct gctactagag ctggagcagg actccggtgt gcaggtcgag     720
gggctgacag tgcagtacct gggccaggcg cctgagctgc tgggtggagc agagcctggc     780
acctacctga ctggcaccat caatggagat ccggagtcgg tggcatctct gcactgggat     840
gggggagccc tgttaggcgt gttacaatat cgggggggctg aactccacct ccagcccctg     900
gagggaggca cccctaactc tgctggggga cctgggggctc acatcctacg ccggaagagt     960
cctgccagcg gtcaaggtcc catgtgcaac gtcaaggctc tcttggaag ccccagcccc    1020 agaccccgaa gagccaagcg ctttgcttca ctgagtagat tgtgggagac actggtggtg    1080
gcagatgaca agatggccgc attccacggt gcggggctaa agcgctacct gctaacagtg    1140
atggcagcag cagccaaggc cttcaagcac ccaagcatcc gcaatcctgt cagcttggtg    1200
gtgactcggc tagtgatcct ggggtcaggc gaggaggggc cccaagtggg gcccagtgct    1260
gcccagaccc tgcgcagctt ctgtgcctgg cagcggggcc tcaacacccc tgaggactcg    1320
gaccctgacc acttttgacac agccattctg tttacccgtc aggacctgtg tggagtctcc    1380
acttgcgaca cgctgggtat ggctgatgtg ggcaccgtct gtgacccggc tcggagctgt    1440
gccattgtgg aggatgatgg gctccagtca gccttcactg ctgctcatga actgggtcat    1500
gtcttcaaca tgctccatga caactccaag ccatgcatca gtttgaatgg gccttttgagc    1560 acctctcgcc atgtcatggc ccctgtgatg gctcatgtgg atcctgagga gccctggtcc    1620
ccctgcagtg cccgcttcat cactgacttc ctggacaatg gctatgggca ctgtctctta    1680
gacaaaccag aggctccatt gcatctgcct gtgactttcc ctggcaagga ctatgatgct    1740
```

-continued

```
gaccgccagt gccagctgac cttcgggccc gactcacgcc attgtccaca gctgccgccg       1800
ccctgtgctg ccctctggtg ctctggccac ctcaatggcc atgccatgtg ccagaccaaa       1860
cactcgccct gggccgatgg cacaccctgc gggcccgcac aggcctgcat gggtggtcgc       1920
tgcctccaca tggaccagct ccaggacttc aatattccac aggctggtgg ctgggggtcct      1980 tggggaccat ggggtgactg ctctcggacc tgtgggggtg gtgtccagtt ctcctcccga       2040
gactgcacga ggcctgtccc ccggaatggt ggcaagtact gtgagggccg ccgtacccgc       2100
ttccgctcct gcaacactga ggactgccca actggctcag ccctgacctt ccgcaggag        2160 cagtgtgctg cctacaacca ccgcaccgac ctcttcaaga gcttcccagg gcccatggac       2220
tgggttcctc gctacacagg cgtggccccc caggaccagt gcaaactcac ctgccaggcc       2280
cgggcactgg gctactacta tgtgctggag ccacgggtgg tagatgggac ccctgttcc        2340 ccggacagct cctcggtctg tgtccagggc cgatgcatcc atgctggctg tgatcgcatc       2400
attggctcca agaagaagtt tgacaagtgc atggtgtgcg gaggggacgg ttctggttgc       2460
agcaagcagt caggctcctt caggaaattc aggtacggat acaacaatgt ggtcactatc       2520
cccgcggggg ccacccacat tcttgtccgg cagcagggaa accctggcca ccggagcatc       2580
tacttggccc tgaagctgcc agatggctcc tatgccctca atggtgaata cacgctgatg       2640
ccctccccca cagatgtggt actgcctggg gcagtcagct gcgctacag cggggccact         2700 gcagcctcag agacactgtc aggccatggg ccactggccc agcctttgac actgcaagtc       2760
ctagtggctg caaccccca ggacacacgc ctccgataca gcttcttcgt gccccggccg         2820 acccccttcaa cgccacgccc cactccccag gactggctgc accgaagagc acagattctg      2880
gagatccttc ggcggcgccc ctgggcgggc aggaaataac ctcactatcc cggctgccct       2940
ttctgggcac cggggcctcg gacttagctg ggagaaagag agagcttctg ttgctgcctc       3000
atgctaagac tcagtgggga ggggctgtgg gcgtgagacc tgcccctcct ctctgcccta       3060
atgcgcaggc tggccctgcc ctggtttcct gccctgggag gcagtgatgg gttagtggat       3120
ggaaggggct gacagacagc cctccatcta aactgccccc tctgccctgc gggtcacagg       3180
agggaggggg aaggcaggga gggcctgggc cccagttgta tttatttagt atttattcac       3240
ttttatttag caccagggaa ggggacaagg actagggtcc tggggaacct gaccctgac        3300 ccctcatagc cctcaccctg gggctaggaa atccagggtg gtggtgatag gtataagtgg       3360
tgtgtgtatg cgtgtgtgtg tgtgtgtgaa aatgtgtgtg tgcttatgta tgaggtacaa       3420
cctgttctgc tttcctcttc ctgaattta tttttggga aaagaaaagt caagggtagg          3480
gtgggccttc agggagtgag ggattatcct tttttttttc tttctttctt tcttttttttt      3540 tttgagacag aatctcgctc tgtcgcccag gctggagtgc aatggcacaa tctcggctca       3600
ctgcatcctc cgcctcccgg gttcaagtga ttctcatgcc tcagcctcct gagtagctgg       3660
gattacaggc tcctgccacc acgcccggct aatttttgtt ttgttttgtt tggagacaga      3720
gtctcgctat tgtcaccagg gctggaatga tttcagctca ctgcaacctt cgccacctgg       3780
gttccagcaa ttctcctgcc tcagcctccc gagtagctga gattataggc acctaccacc       3840
acgcccggct aattttgta tttttagtag agacggggtt tcaccatgtt ggccaggctg       3900
gtctcgaact cctgaccttta ggtgatccac tcgccttcat ctcccaaagt gctgggatta      3960
caggcgtgag ccaccgtgcc tggccacgcc caactaattt ttgtattttt agtagagaca       4020
gggtttcacc atgttggcca ggctgctctt gaactcctga cctcaggtaa tcgacctgcc       4080
```

```
tcggcctccc aaagtgctgg gattacaggt gtgagccacc acgcccggta catattttt    4140 aaattgaatt ctactattta tgtgatcctt ttggagtcag acagatgtgg gt           4192
```

<210> SEQ ID NO 2
<211> LENGTH: 837
<212> TYPE: PRT
<213> ORGANISM: Homo sapiens

<400> SEQUENCE: 2

```
Met Ser Gln Thr Gly Ser His Pro Gly Arg Gly Leu Ala Gly Arg Trp
1               5                   10                  15

Leu Trp Gly Ala Gln Pro Cys Leu Leu Leu Pro Ile Val Pro Leu Ser
            20                  25                  30

Trp Leu Val Trp Leu Leu Leu Leu Leu Ala Ser Leu Leu Pro Ser
        35                  40                  45

Ala Arg Leu Ala Ser Pro Leu Pro Arg Glu Glu Glu Ile Val Phe Pro
    50                  55                  60

Glu Lys Leu Asn Gly Ser Val Leu Pro Gly Ser Gly Ala Pro Ala Arg
65                  70                  75                  80

Leu Leu Cys Arg Leu Gln Ala Phe Gly Glu Thr Leu Leu Leu Glu Leu
                85                  90                  95

Glu Gln Asp Ser Gly Val Gln Val Glu Gly Leu Thr Val Gln Tyr Leu
            100                 105                 110

Gly Gln Ala Pro Glu Leu Leu Gly Gly Ala Glu Pro Gly Thr Tyr Leu
        115                 120                 125

Thr Gly Thr Ile Asn Gly Asp Pro Glu Ser Val Ala Ser Leu His Trp
130                 135                 140

Asp Gly Gly Ala Leu Leu Gly Val Leu Gln Tyr Arg Gly Ala Glu Leu
145                 150                 155                 160

His Leu Gln Pro Leu Glu Gly Gly Thr Pro Asn Ser Ala Gly Gly Pro
                165                 170                 175

Gly Ala His Ile Leu Arg Arg Lys Ser Pro Ala Ser Gly Gln Gly Pro
            180                 185                 190

Met Cys Asn Val Lys Ala Pro Leu Gly Ser Pro Ser Pro Arg Pro Arg
        195                 200                 205

Arg Ala Lys Arg Phe Ala Ser Leu Ser Arg Phe Val Glu Thr Leu Val
    210                 215                 220

Val Ala Asp Asp Lys Met Ala Ala Phe His Gly Ala Gly Leu Lys Arg
225                 230                 235                 240

Tyr Leu Leu Thr Val Met Ala Ala Ala Lys Ala Phe Lys His Pro
                245                 250                 255

Ser Ile Arg Asn Pro Val Ser Leu Val Val Thr Arg Leu Val Ile Leu
            260                 265                 270

Gly Ser Gly Glu Glu Gly Pro Gln Val Gly Pro Ser Ala Ala Gln Thr
        275                 280                 285

Leu Arg Ser Phe Cys Ala Trp Gln Arg Gly Leu Asn Thr Pro Glu Asp
    290                 295                 300

Ser Asp Pro Asp His Phe Asp Thr Ala Ile Leu Phe Thr Arg Gln Asp
305                 310                 315                 320

Leu Cys Gly Val Ser Thr Cys Asp Thr Leu Gly Met Ala Asp Val Gly
                325                 330                 335

Thr Val Cys Asp Pro Ala Arg Ser Cys Ala Ile Val Glu Asp Asp Gly
            340                 345                 350
```

```
Leu Gln Ser Ala Phe Thr Ala Ala His Glu Leu Gly His Val Phe Asn
        355                 360                 365
Met Leu His Asp Asn Ser Lys Pro Cys Ile Ser Leu Asn Gly Pro Leu
        370                 375                 380
Ser Thr Ser Arg His Val Met Ala Pro Val Met Ala His Val Asp Pro
385                 390                 395                 400
Glu Glu Pro Trp Ser Pro Cys Ser Ala Arg Phe Ile Thr Asp Phe Leu
                405                 410                 415
Asp Asn Gly Tyr Gly His Cys Leu Leu Asp Lys Pro Glu Ala Pro Leu
                420                 425                 430
His Leu Pro Val Thr Phe Pro Gly Lys Asp Tyr Asp Ala Asp Arg Gln
        435                 440                 445
Cys Gln Leu Thr Phe Gly Pro Asp Ser Arg His Cys Pro Gln Leu Pro
        450                 455                 460
Pro Pro Cys Ala Ala Leu Trp Cys Ser Gly His Leu Asn Gly His Ala
465                 470                 475                 480
Met Cys Gln Thr Lys His Ser Pro Trp Ala Asp Gly Thr Pro Cys Gly
                485                 490                 495
Pro Ala Gln Ala Cys Met Gly Gly Arg Cys Leu His Met Asp Gln Leu
                500                 505                 510
Gln Asp Phe Asn Ile Pro Gln Ala Gly Gly Trp Gly Pro Trp Gly Pro
        515                 520                 525
Trp Gly Asp Cys Ser Arg Thr Cys Gly Gly Gly Val Gln Phe Ser Ser
        530                 535                 540
Arg Asp Cys Thr Arg Pro Val Pro Arg Asn Gly Gly Lys Tyr Cys Glu
545                 550                 555                 560
Gly Arg Arg Thr Arg Phe Arg Ser Cys Asn Thr Glu Asp Cys Pro Thr
                565                 570                 575
Gly Ser Ala Leu Thr Phe Arg Glu Glu Gln Cys Ala Ala Tyr Asn His
                580                 585                 590
Arg Thr Asp Leu Phe Lys Ser Phe Pro Gly Pro Met Asp Trp Val Pro
        595                 600                 605
Arg Tyr Thr Gly Val Ala Pro Gln Asp Gln Cys Lys Leu Thr Cys Gln
        610                 615                 620
Ala Arg Ala Leu Gly Tyr Tyr Val Leu Glu Pro Arg Val Val Asp
625                 630                 635                 640
Gly Thr Pro Cys Ser Pro Asp Ser Ser Val Cys Val Gln Gly Arg
                645                 650                 655
Cys Ile His Ala Gly Cys Asp Arg Ile Ile Gly Ser Lys Lys Phe
                660                 665                 670
Asp Lys Cys Met Val Cys Gly Gly Asp Gly Ser Gly Cys Ser Lys Gln
        675                 680                 685
Ser Gly Ser Phe Arg Lys Phe Arg Tyr Gly Tyr Asn Asn Val Val Thr
        690                 695                 700
Ile Pro Ala Gly Ala Thr His Ile Leu Val Arg Gln Gln Gly Asn Pro
705                 710                 715                 720
Gly His Arg Ser Ile Tyr Leu Ala Leu Lys Leu Pro Asp Gly Ser Tyr
                725                 730                 735
Ala Leu Asn Gly Glu Tyr Thr Leu Met Pro Ser Pro Thr Asp Val Val
                740                 745                 750
Leu Pro Gly Ala Val Ser Leu Arg Tyr Ser Gly Ala Thr Ala Ala Ser
        755                 760                 765
```

-continued

```
Glu Thr Leu Ser Gly His Gly Pro Leu Ala Gln Pro Leu Thr Leu Gln
    770             775                 780

Val Leu Val Ala Gly Asn Pro Gln Asp Thr Arg Leu Arg Tyr Ser Phe
785             790                 795                 800

Phe Val Pro Arg Pro Thr Pro Ser Thr Pro Arg Pro Thr Pro Gln Asp
                805                 810                 815

Trp Leu His Arg Arg Ala Gln Ile Leu Glu Ile Leu Arg Arg Pro
            820                 825                 830

Trp Ala Gly Arg Lys
        835

<210> SEQ ID NO 3

<400> SEQUENCE: 3

000

<210> SEQ ID NO 4
<211> LENGTH: 26
<212> TYPE: PRT
<213> ORGANISM: Bos taurus

<400> SEQUENCE: 4

Phe Ala Ser Leu Ser Arg Val Glu Thr Leu Val Val Ala Asp Asp Lys
1               5                   10                  15

Met Ala Ala Phe His Gly Ala Gly Leu Lys
            20                  25

<210> SEQ ID NO 5
<211> LENGTH: 7
<212> TYPE: PRT
<213> ORGANISM: Bos taurus

<400> SEQUENCE: 5

Tyr Thr Gly Val Ala Pro Arg
1               5

<210> SEQ ID NO 6
<211> LENGTH: 11
<212> TYPE: PRT
<213> ORGANISM: Bos taurus

<400> SEQUENCE: 6

Ala Leu Gly Tyr Tyr Tyr Val Leu Asp Pro Arg
1               5                   10

<210> SEQ ID NO 7
<211> LENGTH: 21
<212> TYPE: DNA
<213> ORGANISM: Mus musculus

<400> SEQUENCE: 7
gggggtggtg tccagttctc c                                        21

<210> SEQ ID NO 8
<211> LENGTH: 23
<212> TYPE: DNA
<213> ORGANISM: Mus musculus

<400> SEQUENCE: 8
ggccctggaa agctcttgaa gag                                      23
```

```
<210> SEQ ID NO 9
<211> LENGTH: 23
<212> TYPE: DNA
<213> ORGANISM: Homo sapiens

<400> SEQUENCE: 9
ccccggaatg gtggcaagta ctg                                          23

<210> SEQ ID NO 10
<211> LENGTH: 23
<212> TYPE: DNA
<213> ORGANISM: Homo sapiens

<400> SEQUENCE: 10
acccacatct gtctgactcc aaa                                          23

<210> SEQ ID NO 11
<211> LENGTH: 23
<212> TYPE: DNA
<213> ORGANISM: Homo sapiens

<400> SEQUENCE: 11
ccagttgggc agtcctcagt gtt                                          23

<210> SEQ ID NO 12
<211> LENGTH: 22
<212> TYPE: DNA
<213> ORGANISM: Homo sapiens

<400> SEQUENCE: 12
ggtcggtgcg gtggttgtag gc                                           22

<210> SEQ ID NO 13
<211> LENGTH: 17
<212> TYPE: PRT
<213> ORGANISM: Homo sapiens

<400> SEQUENCE: 13

Cys Ala Ser Leu Ser Arg Phe Val Glu Thr Leu Val Val Ala Asp Asp
1               5                   10                  15

Lys

<210> SEQ ID NO 14
<211> LENGTH: 3250
<212> TYPE: DNA
<213> ORGANISM: Homo sapiens

<400> SEQUENCE: 14
tgactcaatc ctgcaagcaa gtgtgtgtgt gtccccatcc cccgccccgt taacttcata     60
gcaaataaca aatacccata aagtcccagt cgcgcagccc ctccccgcgg gcagcgcact    120
atgctgctcg ggtgggcgtc cctgctgctg tgcgcgttcc gcctgccccct ggccgcggtc    180 ggccccgccg cgacacctgc ccaggataaa gccgggcagc ctccgactgc tgcagcagcc    240
gcccagcccc gccggcggca gggggaggag gtgcaggagc gagccgagcc tcccggccac    300
ccgcaccccc tggcgcagcg gcgcaggagc aaggggctgg tgcagaacat cgaccaactc    360
tactccggcg gcggcaaggt gggctacctc gtctacgcgg gcggccggag gttcctcttg    420
gacctggagc gagatggttc ggtgggcatt gctggcttcg tgcccgcagg aggcgggacg    480
agtgcgccct ggcgccaccg gagccactgc ttctatcggg gcacagtgga cgctagtccc    540
cgctctctgg ctgtctttga cctctgtggg ggtctcgacg gcttcttcgc ggtcaagcac    600
```

-continued

| | |
|---|---|
| gcgcgctaca cccctaaagcc actgctgcgc ggaccctggg cggaggaaga aaagggggcgc | 660 |
| gtgtacgggg atgggtccgc acggatcctg cacgtctaca cccgcgaggg cttcagcttc | 720 |
| gaggccctgc cgccgcgcgc cagctgcgaa accccgcgt ccacaccgga ggcccacgag | 780 |
| catgctccgg cgcacagcaa cccgagcgga cgcgcagcac tggcctcgca gctcttggac | 840 |
| cagtccgctc tctcgcccgc tgggggctca ggaccgcaga cgtggtggcg gcggcggcgc | 900 |
| cgctccatct cccgggcccg ccaggtggag ctgcttctgg tggctgacgc gtccatggcg | 960 |
| cggttgtatg gccggggcct gcagcattac ctgctgaccc tggcctccat cgccaatagg | 1020 |
| ctgtacagcc atgctagcat cgagaaccac atccgcctgg ccgtggtgaa ggtggtggtg | 1080 |
| ctaggcgaca aggacaagag cctggaagtg agcaagaacg ctgccaccac actcaagaac | 1140 |
| ttttgcaagt ggcagcacca acacaaccag ctgggagatg accatgagga gcactacgat | 1200 |
| gcagctatcc tgtttactcg ggaggattta tgtgggcatc attcatgtga caccctggga | 1260 |
| atggcagacg ttgggaccat atgttctcca gagcgcagct gtgctgtgat tgaagacgat | 1320 |
| ggcctccacg cagccttcac tgtggctcac gaaatcggac atttacttgg cctctcccat | 1380 |
| gacgattcca aattctgtga agagaccttt ggttccacag aagataagcg cttaatgtct | 1440 |
| tccatcctta ccagcattga tgcatctaag ccctggtcca aatgcacttc agccaccatc | 1500 |
| acagaattcc tggatgatgg ccatggtaac tgtttgctgg acctaccacg aaagcagatc | 1560 |
| ctgggccccg aagaactccc aggacagacc tacgatgcca cccagcagtg caacctgaca | 1620 |
| ttcgggcctg agtactccgt gtgtcccggc atggatgtct gtgctcgcct gtggtgtgct | 1680 |
| gtggtacgcc agggccagat ggtctgtctg accaagaagc tgcctgcggt ggaagggacg | 1740 |
| ccttgtggaa aggggagaat ctgcctgcag ggcaaatgtg tggacaaaac caagaaaaaa | 1800 |
| tattattcaa cgtcaagcca tggcaactgg ggatcttggg gatcctgggg ccagtgttct | 1860 |
| cgctcatgtg gaggaggagt gcagtttgcc tatcgtcact gtaataaccc tgctcccaga | 1920 |
| aacaacggac gctactgcac agggaagagg gccatctacc gctcctgcag tctcatgccc | 1980 |
| tgccccaccca atggtaaatc atttcgtcat gaacagtgtg aggccaaaaa tggctatcag | 2040 |
| tctgatgcaa aaggagtcaa aactttttgtg gaatgggttc ccaaatatgc aggtgtcctg | 2100 |
| ccagcggatg tgtgcaagct gacctgcaga gccaagggca ctggctacta tgtggtattt | 2160 |
| tctccaaagg tgaccgatgg cactgaatgt aggccgtaca gtaattccgt ctgcgtccgg | 2220 |
| gggaagtgtg tgagaactgg ctgtgacggc atcattggct caaagctgca gtatgacaag | 2280 |
| tgcggagtat gtgaggagag caactccagc tgtacaaaga ttgttggaac ctttaataag | 2340 |
| aaaagtaagg gttacactga cgtggtgagg attcctgaag gggcaaccca cataaaagtt | 2400 |
| cgacagttca agccaaaga ccagactaga ttcactgcct atttagccct gaaaaagaaa | 2460 |
| aacggtgagt accttatcaa tggaaagtac atgatctcca cttcagagac tatcattgac | 2520 |
| atcaatggaa cagtcatgaa ctatagcggt tggagccaca gggatgactt cctgcatggc | 2580 |
| atgggctact ctgccacgaa ggaaattcta atagtgcaga ttcttgcaac agaccccact | 2640 |
| aaaccattag atgtccgtta tagctttttt gttcccaaga agtccactcc aaaagtaaac | 2700 |
| tctgtcacta gtcatggcag caataaagtg ggatcacaca cttcgcagcc gcagtgggtc | 2760 |
| acgggcccat ggctcgcctg ctctaggacc tgtgacacag gttggcacac cagaacggtg | 2820 |
| cagtgccagg atggaaaccg gaagttagca aaaggatgtc ctctctccca aaggccttct | 2880 |
| gcgtttaagc aatgcttgtt gaagaaatgt tagcctgtgg ttatgatctt atgcacaaag | 2940 |
| ataactggag gattcagcac cgatgcagtc gtggtgaaca ggaggtctac ctaacgcaca | 3000 |

-continued

```
gaaagtcatg cttcagtgac attgtcaaca ggagtccaat tatgggcaga atctgctctc    3060
tgtgaccaaa agaggatgtg cactgcttca cgtgacagtg gtgaccttgc aatatagaaa    3120
aacttgggag ttattgaaca tccctggga ttacaagaaa cactgatgaa tgttaaatca     3180
ggggacattt gaagatggca gaactgtctc ccccttgtca cctacctctg aatagaatgt    3240
ctttaatggt                                                            3250
```

<210> SEQ ID NO 15
<211> LENGTH: 930
<212> TYPE: PRT
<213> ORGANISM: Homo sapiens

<400> SEQUENCE: 15

| Met | Leu | Leu | Gly | Trp | Ala | Ser | Leu | Leu | Cys | Ala | Phe | Arg | Leu | Pro |
| 1 | | | | 5 | | | | | 10 | | | | | 15 |

| Leu | Ala | Ala | Val | Gly | Pro | Ala | Ala | Thr | Pro | Ala | Gln | Asp | Lys | Ala | Gly |
| | | | 20 | | | | | 25 | | | | | 30 | | |

| Gln | Pro | Pro | Thr | Ala | Ala | Ala | Ala | Gln | Pro | Arg | Arg | Arg | Gln | Gly |
| | | 35 | | | | | 40 | | | | | 45 | | |

| Glu | Glu | Val | Gln | Glu | Arg | Ala | Glu | Pro | Pro | Gly | His | Pro | His | Pro | Leu |
| 50 | | | | | | 55 | | | | | 60 | | | | |

| Ala | Gln | Arg | Arg | Ser | Lys | Gly | Leu | Val | Gln | Asn | Ile | Asp | Gln | Leu |
| 65 | | | | 70 | | | | | 75 | | | | | 80 |

| Tyr | Ser | Gly | Gly | Gly | Lys | Val | Gly | Tyr | Leu | Val | Tyr | Ala | Gly | Gly | Arg |
| | | | | 85 | | | | | 90 | | | | | 95 | |

| Arg | Phe | Leu | Leu | Asp | Leu | Glu | Arg | Asp | Gly | Ser | Val | Gly | Ile | Ala | Gly |
| | | | 100 | | | | | 105 | | | | | 110 | | |

| Phe | Val | Pro | Ala | Gly | Gly | Thr | Ser | Ala | Pro | Trp | Arg | His | Arg | Ser |
| | | 115 | | | | | 120 | | | | | 125 | | |

| His | Cys | Phe | Tyr | Arg | Gly | Thr | Val | Asp | Ala | Ser | Pro | Arg | Ser | Leu | Ala |
| | 130 | | | | | 135 | | | | | 140 | | | | |

| Val | Phe | Asp | Leu | Cys | Gly | Gly | Leu | Asp | Gly | Phe | Phe | Ala | Val | Lys | His |
| 145 | | | | 150 | | | | | 155 | | | | | 160 | |

| Ala | Arg | Tyr | Thr | Leu | Lys | Pro | Leu | Leu | Arg | Gly | Pro | Trp | Ala | Glu | Glu |
| | | | 165 | | | | | 170 | | | | | 175 | | |

| Glu | Lys | Gly | Arg | Val | Tyr | Gly | Asp | Gly | Ser | Ala | Arg | Ile | Leu | His | Val |
| | | | 180 | | | | | 185 | | | | | 190 | | |

| Tyr | Thr | Arg | Glu | Gly | Phe | Ser | Phe | Glu | Ala | Leu | Pro | Pro | Arg | Ala | Ser |
| | | 195 | | | | | 200 | | | | | 205 | | | |

| Cys | Glu | Thr | Pro | Ala | Ser | Thr | Pro | Glu | Ala | His | Glu | His | Ala | Pro | Ala |
| | 210 | | | | | 215 | | | | | 220 | | | | |

| His | Ser | Asn | Pro | Ser | Gly | Arg | Ala | Ala | Leu | Ala | Ser | Gln | Leu | Leu | Asp |
| 225 | | | | 230 | | | | | 235 | | | | | 240 | |

| Gln | Ser | Ala | Leu | Ser | Pro | Ala | Gly | Gly | Ser | Gly | Pro | Gln | Thr | Trp | Trp |
| | | | 245 | | | | | 250 | | | | | 255 | | |

| Arg | Arg | Arg | Arg | Arg | Ser | Ile | Ser | Arg | Ala | Arg | Gln | Val | Glu | Leu | Leu |
| | | | 260 | | | | | 265 | | | | | 270 | | |

| Leu | Val | Ala | Asp | Ala | Ser | Met | Ala | Arg | Leu | Tyr | Gly | Arg | Gly | Leu | Gln |
| | | 275 | | | | | 280 | | | | | 285 | | | |

| His | Tyr | Leu | Leu | Thr | Leu | Ala | Ser | Ile | Ala | Asn | Arg | Leu | Tyr | Ser | His |
| | 290 | | | | | 295 | | | | | 300 | | | | |

| Ala | Ser | Ile | Glu | Asn | His | Ile | Arg | Leu | Ala | Val | Val | Lys | Val | Val |
| 305 | | | | 310 | | | | | 315 | | | | | 320 |

```
Leu Gly Asp Lys Asp Lys Ser Leu Glu Val Ser Lys Asn Ala Ala Thr
                325                 330                 335
Thr Leu Lys Asn Phe Cys Lys Trp Gln His Gln His Asn Gln Leu Gly
                340                 345                 350
Asp Asp His Glu His Tyr Asp Ala Ala Ile Leu Phe Thr Arg Glu
                355                 360                 365
Asp Leu Cys Gly His His Ser Cys Asp Thr Leu Gly Met Ala Asp Val
    370                 375                 380
Gly Thr Ile Cys Ser Pro Glu Arg Ser Cys Ala Val Ile Glu Asp Asp
385                 390                 395                 400
Gly Leu His Ala Ala Phe Thr Val Ala His Glu Ile Gly His Leu Leu
                405                 410                 415
Gly Leu Ser His Asp Asp Ser Lys Phe Cys Glu Glu Thr Phe Gly Ser
                420                 425                 430
Thr Glu Asp Lys Arg Leu Met Ser Ser Ile Leu Thr Ser Ile Asp Ala
                435                 440                 445
Ser Lys Pro Trp Ser Lys Cys Thr Ser Ala Thr Ile Thr Glu Phe Leu
    450                 455                 460
Asp Asp Gly His Gly Asn Cys Leu Leu Asp Leu Pro Arg Lys Gln Ile
465                 470                 475                 480
Leu Gly Pro Glu Glu Leu Pro Gly Gln Thr Tyr Asp Ala Thr Gln Gln
                485                 490                 495
Cys Asn Leu Thr Phe Gly Pro Glu Tyr Ser Val Cys Pro Gly Met Asp
                500                 505                 510
Val Cys Ala Arg Leu Trp Cys Ala Val Val Arg Gln Gly Gln Met Val
                515                 520                 525
Cys Leu Thr Lys Lys Leu Pro Ala Val Glu Gly Thr Pro Cys Gly Lys
    530                 535                 540
Gly Arg Ile Cys Leu Gln Gly Lys Cys Val Asp Lys Thr Lys Lys Lys
545                 550                 555                 560
Tyr Tyr Ser Thr Ser Ser His Gly Asn Trp Gly Ser Trp Gly Ser Trp
                565                 570                 575
Gly Gln Cys Ser Arg Ser Cys Gly Gly Gly Val Gln Phe Ala Tyr Arg
                580                 585                 590
His Cys Asn Asn Pro Ala Pro Arg Asn Asn Gly Arg Tyr Cys Thr Gly
                595                 600                 605
Lys Arg Ala Ile Tyr Arg Ser Cys Ser Leu Met Pro Cys Pro Pro Asn
                610                 615                 620
Gly Lys Ser Phe Arg His Glu Gln Cys Glu Ala Lys Asn Gly Tyr Gln
625                 630                 635                 640
Ser Asp Ala Lys Gly Val Lys Thr Phe Val Glu Trp Val Pro Lys Tyr
                645                 650                 655
Ala Gly Val Leu Pro Ala Asp Val Cys Lys Leu Thr Cys Arg Ala Lys
                660                 665                 670
Gly Thr Gly Tyr Tyr Val Val Phe Ser Pro Lys Val Thr Asp Gly Thr
                675                 680                 685
Glu Cys Arg Pro Tyr Ser Asn Ser Val Cys Val Arg Gly Lys Cys Val
                690                 695                 700
Arg Thr Gly Cys Asp Gly Ile Ile Gly Ser Lys Leu Gln Tyr Asp Lys
705                 710                 715                 720
Cys Gly Val Cys Gly Gly Asp Asn Ser Ser Cys Thr Lys Ile Val Gly
                725                 730                 735
```

```
Thr Phe Asn Lys Lys Ser Lys Gly Tyr Thr Asp Val Val Arg Ile Pro
                740                 745                 750

Glu Gly Ala Thr His Ile Lys Val Arg Gln Phe Lys Ala Lys Asp Gln
            755                 760                 765

Thr Arg Phe Thr Ala Tyr Leu Ala Leu Lys Lys Asn Gly Glu Tyr
770                 775                 780

Leu Ile Asn Gly Lys Tyr Met Ile Ser Thr Ser Glu Thr Ile Ile Asp
785                 790                 795                 800

Ile Asn Gly Thr Val Met Asn Tyr Ser Gly Trp Ser His Arg Asp Asp
                805                 810                 815

Phe Leu His Gly Met Gly Tyr Ser Ala Thr Lys Glu Ile Leu Ile Val
            820                 825                 830

Gln Ile Leu Ala Thr Asp Pro Thr Lys Pro Leu Asp Val Arg Tyr Ser
        835                 840                 845

Phe Phe Val Pro Lys Lys Ser Thr Pro Lys Val Asn Ser Val Thr Ser
850                 855                 860

His Gly Ser Asn Lys Val Gly Ser His Thr Ser Gln Pro Gln Trp Val
865                 870                 875                 880

Thr Gly Pro Trp Leu Ala Cys Ser Arg Thr Cys Asp Thr Gly Trp His
                885                 890                 895

Thr Arg Thr Val Gln Cys Gln Asp Gly Asn Arg Lys Leu Ala Lys Gly
            900                 905                 910

Cys Pro Leu Ser Gln Arg Pro Ser Ala Phe Lys Gln Cys Leu Leu Lys
        915                 920                 925

Lys Cys
    930

<210> SEQ ID NO 16
<211> LENGTH: 42
<212> TYPE: PRT
<213> ORGANISM: Homo sapiens

<400> SEQUENCE: 16

Ser Ile Ser Arg Ala Arg Gln Val Glu Leu Leu Val Ala Asp Ala
1               5                   10                  15

Ser Met Ala Arg Met Tyr Gly Arg Gly Leu Gln His Tyr Leu Leu Thr
            20                  25                  30

Leu Ala Ser Ile Ala Asn Lys Leu Tyr Phe
        35                  40

<210> SEQ ID NO 17
<211> LENGTH: 23
<212> TYPE: DNA
<213> ORGANISM: Mus musculus

<400> SEQUENCE: 17
cggccacgac cctcaagaac ttt                                           23

<210> SEQ ID NO 18
<211> LENGTH: 25
<212> TYPE: DNA
<213> ORGANISM: Mus musculus

<400> SEQUENCE: 18
gcatggaggc catcatcttc aatca                                         25
```

```
<210> SEQ ID NO 19
<211> LENGTH: 22
<212> TYPE: DNA
<213> ORGANISM: Homo sapiens

<400> SEQUENCE: 19
gggaggattt atgtgggcat ca                                              22

<210> SEQ ID NO 20
<211> LENGTH: 23
<212> TYPE: DNA
<213> ORGANISM: Homo sapiens

<400> SEQUENCE: 20
gtgcatttgg accagggctt aga                                             23

<210> SEQ ID NO 21
<211> LENGTH: 13
<212> TYPE: PRT
<213> ORGANISM: Artificial Sequence
<220> FEATURE:
<223> OTHER INFORMATION: Synthesized peptide
<220> FEATURE:
<221> NAME/KEY: MISC_FEATURE
<222> LOCATION: (12)..(12)
<223> OTHER INFORMATION: Acp
<220> FEATURE:
<221> NAME/KEY: MOD_RES
<222> LOCATION: (12)..(12)
<223> OTHER INFORMATION: Acp

<400> SEQUENCE: 21

Ser Ile Ser Arg Ala Arg Gln Val Glu Leu Leu Xaa Cys
1               5                   10

<210> SEQ ID NO 22
<211> LENGTH: 14
<212> TYPE: PRT
<213> ORGANISM: homo sapiens

<400> SEQUENCE: 22

Asn Ile Thr Glu Gly Glu Ala Arg Gly Ser Val Ile Leu Thr
1               5                   10

<210> SEQ ID NO 23
<211> LENGTH: 14
<212> TYPE: PRT
<213> ORGANISM: bovine

<400> SEQUENCE: 23

Asn Ile Thr Glu Gly Glu Ala Arg Gly Ser Val Ile Leu Thr
1               5                   10

<210> SEQ ID NO 24
<211> LENGTH: 14
<212> TYPE: PRT
<213> ORGANISM: rat

<400> SEQUENCE: 24

Asn Ile Thr Glu Gly Glu Ala Arg Gly Asn Val Ile Leu Thr
1               5                   10

<210> SEQ ID NO 25
<211> LENGTH: 14
<212> TYPE: PRT
<213> ORGANISM: mouse
```

```
<400> SEQUENCE: 25

Asn Val Thr Glu Gly Glu Ala Leu Gly Ser Val Ile Leu Thr
1               5                  10

<210> SEQ ID NO 26
<211> LENGTH: 14
<212> TYPE: PRT
<213> ORGANISM: pig

<400> SEQUENCE: 26

Asn Ile Thr Glu Gly Glu Ala Arg Gly Thr Val Ile Leu Thr
1               5                  10

<210> SEQ ID NO 27
<211> LENGTH: 14
<212> TYPE: PRT
<213> ORGANISM: sheep

<400> SEQUENCE: 27

Asn Ile Thr Glu Gly Glu Ala Arg Gly Asn Val Ile Leu Thr
1               5                  10

<210> SEQ ID NO 28
<211> LENGTH: 11
<212> TYPE: PRT
<213> ORGANISM: chicken

<400> SEQUENCE: 28

Asn Val Thr Glu Glu Glu Ala Arg Gly Ser Ile
1               5                  10

<210> SEQ ID NO 29
<211> LENGTH: 14
<212> TYPE: PRT
<213> ORGANISM: horse

<400> SEQUENCE: 29

Asn Ile Thr Glu Gly Glu Ala Arg Gly Asn Val Ile Leu Thr
1               5                  10

<210> SEQ ID NO 30
<211> LENGTH: 16
<212> TYPE: PRT
<213> ORGANISM: homo sapiens

<400> SEQUENCE: 30

Ala Ser Thr Ala Ser Glu Leu Glu Gly Arg Gly Thr Ile Gly Ile Ser
1               5                  10                  15

<210> SEQ ID NO 31
<211> LENGTH: 16
<212> TYPE: PRT
<213> ORGANISM: bovine

<400> SEQUENCE: 31

Ala Thr Thr Ala Gly Glu Leu Glu Gly Arg Gly Thr Ile Asp Ile Ser
1               5                  10                  15

<210> SEQ ID NO 32
<211> LENGTH: 16
<212> TYPE: PRT
<213> ORGANISM: mouse
```

```
<400> SEQUENCE: 32

Ala Thr Thr Ser Ser Glu Leu Glu Gly Arg Gly Thr Ile Gly Ile Ser
1               5                   10                  15

<210> SEQ ID NO 33
<211> LENGTH: 16
<212> TYPE: PRT
<213> ORGANISM: rat

<400> SEQUENCE: 33

Ala Thr Thr Ala Ser Glu Leu Glu Gly Arg Gly Thr Ile Ser Val Ser
1               5                   10                  15

<210> SEQ ID NO 34
<211> LENGTH: 16
<212> TYPE: PRT
<213> ORGANISM: homo sapiens

<400> SEQUENCE: 34

Pro Thr Thr Phe Lys Glu Glu Glu Gly Leu Gly Ser Val Glu Leu Ser
1               5                   10                  15

<210> SEQ ID NO 35
<211> LENGTH: 16
<212> TYPE: PRT
<213> ORGANISM: bovine

<400> SEQUENCE: 35

Pro Thr Thr Phe Lys Glu Glu Glu Gly Leu Gly Ser Val Glu Leu Ser
1               5                   10                  15

<210> SEQ ID NO 36
<211> LENGTH: 16
<212> TYPE: PRT
<213> ORGANISM: rat

<400> SEQUENCE: 36

Pro Thr Thr Phe Arg Glu Glu Glu Gly Leu Gly Ser Val Glu Leu Ser
1               5                   10                  15

<210> SEQ ID NO 37
<211> LENGTH: 16
<212> TYPE: PRT
<213> ORGANISM: mouse

<400> SEQUENCE: 37

Pro Thr Thr Phe Arg Glu Glu Glu Gly Leu Gly Ser Val Glu Leu Ser
1               5                   10                  15

<210> SEQ ID NO 38
<211> LENGTH: 16
<212> TYPE: PRT
<213> ORGANISM: homo sapiens

<400> SEQUENCE: 38

Thr Gln Ala Pro Thr Ala Gln Glu Ala Gly Glu Gly Pro Ser Gly Ile
1               5                   10                  15

<210> SEQ ID NO 39
<211> LENGTH: 16
<212> TYPE: PRT
<213> ORGANISM: bovine
```

-continued

```
<400> SEQUENCE: 39

Thr Gln Ala Pro Thr Ala Gln Glu Ala Gly Glu Gly Pro Ser Gly Ile
1               5                   10                  15

<210> SEQ ID NO 40
<211> LENGTH: 16
<212> TYPE: PRT
<213> ORGANISM: rat

<400> SEQUENCE: 40

Thr Leu Ala Pro Thr Ala Gln Glu Ala Gly Glu Gly Pro Ser Ser Ile
1               5                   10                  15

<210> SEQ ID NO 41
<211> LENGTH: 16
<212> TYPE: PRT
<213> ORGANISM: mouse

<400> SEQUENCE: 41

Thr Gln Ala Pro Thr Ala Gln Glu Ala Gly Glu Gly Pro Ser Gly Ile
1               5                   10                  15

<210> SEQ ID NO 42
<211> LENGTH: 16
<212> TYPE: PRT
<213> ORGANISM: chicken

<400> SEQUENCE: 42

Thr Gln Thr Ser Val Ala Gln Glu Val Gly Glu Gly Pro Ser Gly Met
1               5                   10                  15

<210> SEQ ID NO 43
<211> LENGTH: 17
<212> TYPE: PRT
<213> ORGANISM: homo sapiens

<400> SEQUENCE: 43

Thr Glu Pro Thr Ile Ser Gln Glu Leu Leu Gly Gln Arg Pro Pro Val
1               5                   10                  15
Thr

<210> SEQ ID NO 44
<211> LENGTH: 16
<212> TYPE: PRT
<213> ORGANISM: bovine

<400> SEQUENCE: 44

Thr Glu Pro Thr Val Ser Gln Glu Leu Gly Gln Arg Pro Pro Val Thr
1               5                   10                  15

<210> SEQ ID NO 45
<211> LENGTH: 16
<212> TYPE: PRT
<213> ORGANISM: rat

<400> SEQUENCE: 45

Thr Glu Pro Thr Val Ser Gln Glu Leu Gly His Gly Pro Ser Met Thr
1               5                   10                  15

<210> SEQ ID NO 46
<211> LENGTH: 16
<212> TYPE: PRT
<213> ORGANISM: mouse
```

```
<400> SEQUENCE: 46

Thr Glu Pro Thr Val Ser Gln Glu Leu Gly His Gly Pro Ser Met Thr
1               5                   10                  15

<210> SEQ ID NO 47
<211> LENGTH: 16
<212> TYPE: PRT
<213> ORGANISM: chicken

<400> SEQUENCE: 47

Thr Arg Pro Thr Val Ser Gln Glu Leu Gly Gly Glu Thr Ala Val Thr
1               5                   10                  15

<210> SEQ ID NO 48
<211> LENGTH: 16
<212> TYPE: PRT
<213> ORGANISM: dog

<400> SEQUENCE: 48

Thr Glu Pro Thr Val Ser Gln Glu Leu Ala Gln Arg Pro Pro Val Thr
1               5                   10                  15

<210> SEQ ID NO 49
<211> LENGTH: 5
<212> TYPE: PRT
<213> ORGANISM: Human

<400> SEQUENCE: 49

Ile Thr Glu Gly Glu
1               5

<210> SEQ ID NO 50
<211> LENGTH: 4
<212> TYPE: PRT
<213> ORGANISM: Human

<400> SEQUENCE: 50

Ala Arg Gly Ser
1

<210> SEQ ID NO 51
<211> LENGTH: 4
<212> TYPE: PRT
<213> ORGANISM: Human

<400> SEQUENCE: 51

Ser Glu Leu Glu
1

<210> SEQ ID NO 52
<211> LENGTH: 4
<212> TYPE: PRT
<213> ORGANISM: Human

<400> SEQUENCE: 52

Gly Arg Gly Thr
1

<210> SEQ ID NO 53
<211> LENGTH: 4
<212> TYPE: PRT
<213> ORGANISM: Human
```

-continued

```
<400> SEQUENCE: 53

Lys Glu Glu Glu
1

<210> SEQ ID NO 54
<211> LENGTH: 4
<212> TYPE: PRT
<213> ORGANISM: Human

<400> SEQUENCE: 54

Gly Leu Gly Ser
1

<210> SEQ ID NO 55
<211> LENGTH: 4
<212> TYPE: PRT
<213> ORGANISM: Human

<400> SEQUENCE: 55

Thr Ala Gln Glu
1

<210> SEQ ID NO 56
<211> LENGTH: 4
<212> TYPE: PRT
<213> ORGANISM: Human

<400> SEQUENCE: 56

Ala Gly Glu Gly
1

<210> SEQ ID NO 57
<211> LENGTH: 4
<212> TYPE: PRT
<213> ORGANISM: Human

<400> SEQUENCE: 57

Ile Ser Gln Glu
1

<210> SEQ ID NO 58
<211> LENGTH: 4
<212> TYPE: PRT
<213> ORGANISM: Human

<400> SEQUENCE: 58

Leu Gly Gln Arg
1

<210> SEQ ID NO 59
<211> LENGTH: 7
<212> TYPE: PRT
<213> ORGANISM: Bovine

<400> SEQUENCE: 59

Ala Arg Gly Ser Val Ile Leu
1               5

<210> SEQ ID NO 60
<211> LENGTH: 17
<212> TYPE: PRT
<213> ORGANISM: Artificial
<220> FEATURE:
<223> OTHER INFORMATION: Synthesized
```

```
-continued

<400> SEQUENCE: 60

Cys Ala Ser Leu Ser Arg Phe Val Glu Thr Leu Val Val Ala Asp Asp
1               5                   10                  15

Lys
```